(12) United States Patent
Malecha

(10) Patent No.: US 9,005,426 B2
(45) Date of Patent: Apr. 14, 2015

(54) SYSTEM AND METHOD FOR DETERMINING HEMATOCRIT INSENSITIVE GLUCOSE CONCENTRATION

(71) Applicant: Michael Malecha, Muir of Ord (GB)

(72) Inventor: Michael Malecha, Muir of Ord (GB)

(73) Assignee: Cilag GmbH International, Zug (CH)

( * ) Notice: Subject to any disclaimer, the term of this patent is extended or adjusted under 35 U.S.C. 154(b) by 267 days.

(21) Appl. No.: 13/630,334

(22) Filed: Sep. 28, 2012

(65) Prior Publication Data

US 2014/0090989 A1    Apr. 3, 2014

(51) Int. Cl.
*G01N 27/327*    (2006.01)
*A61B 5/145*    (2006.01)

(52) U.S. Cl.
CPC ........ *A61B 5/14532* (2013.01); *G01N 27/3273* (2013.01)

(58) Field of Classification Search
CPC .................................. G01N 27/3273–27/3274
USPC ......... 204/403.01–403.15; 205/775, 787, 792
See application file for complete search history.

(56) References Cited

U.S. PATENT DOCUMENTS

| 6,179,979 | B1 | 1/2001 | Hodges et al. |
| 6,193,873 | B1 | 2/2001 | Ohara et al. |
| 6,284,125 | B1 | 9/2001 | Hodges et al. |
| 6,413,410 | B1 | 7/2002 | Hodges et al. |
| 6,475,372 | B1 | 11/2002 | Ohara et al. |
| 6,716,577 | B1 | 4/2004 | Yu et al. |
| 6,749,887 | B1 | 6/2004 | Dick et al. |
| 6,863,801 | B2 | 3/2005 | Hodges et al. |
| 6,890,421 | B2 | 5/2005 | Ohara et al. |
| 7,045,046 | B2 | 5/2006 | Chambers et al. |
| 7,291,256 | B2 | 11/2007 | Teodorczyk et al. |
| 7,498,132 | B2 | 3/2009 | Yu et al. |
| 2008/0179197 | A1 | 7/2008 | Wu |
| 2009/0099787 | A1 | 4/2009 | Carpenter et al. |
| 2011/0108440 | A1 | 5/2011 | Wu et al. |
| 2011/0162978 | A1 | 7/2011 | Cardosi et al. |
| 2011/0297557 | A1 | 12/2011 | Wu et al. |

FOREIGN PATENT DOCUMENTS

WO    WO 2012/084194 A1    6/2012

OTHER PUBLICATIONS

International Application No. PCT/EP2013/070298, International Search Report and Written Opinion dated Jan. 7, 2014, 12 pages, International Searching Authority.
International Application No. PCT/EP2013/070296, International Search Report and Written Opinion dated Jan. 7, 2014, 11 pages, International Searching Authority.

*Primary Examiner* — J. Christopher Ball

(57) ABSTRACT

Described are methods and systems to apply a plurality of test voltages to the test strip and measure at least a current transient output resulting from an electrochemical reaction in a test chamber of the test strip so that a glucose concentration can be determined that are generally insensitive to other substances in the body fluid sample that could affect the precision and accuracy of the glucose concentration.

16 Claims, 14 Drawing Sheets

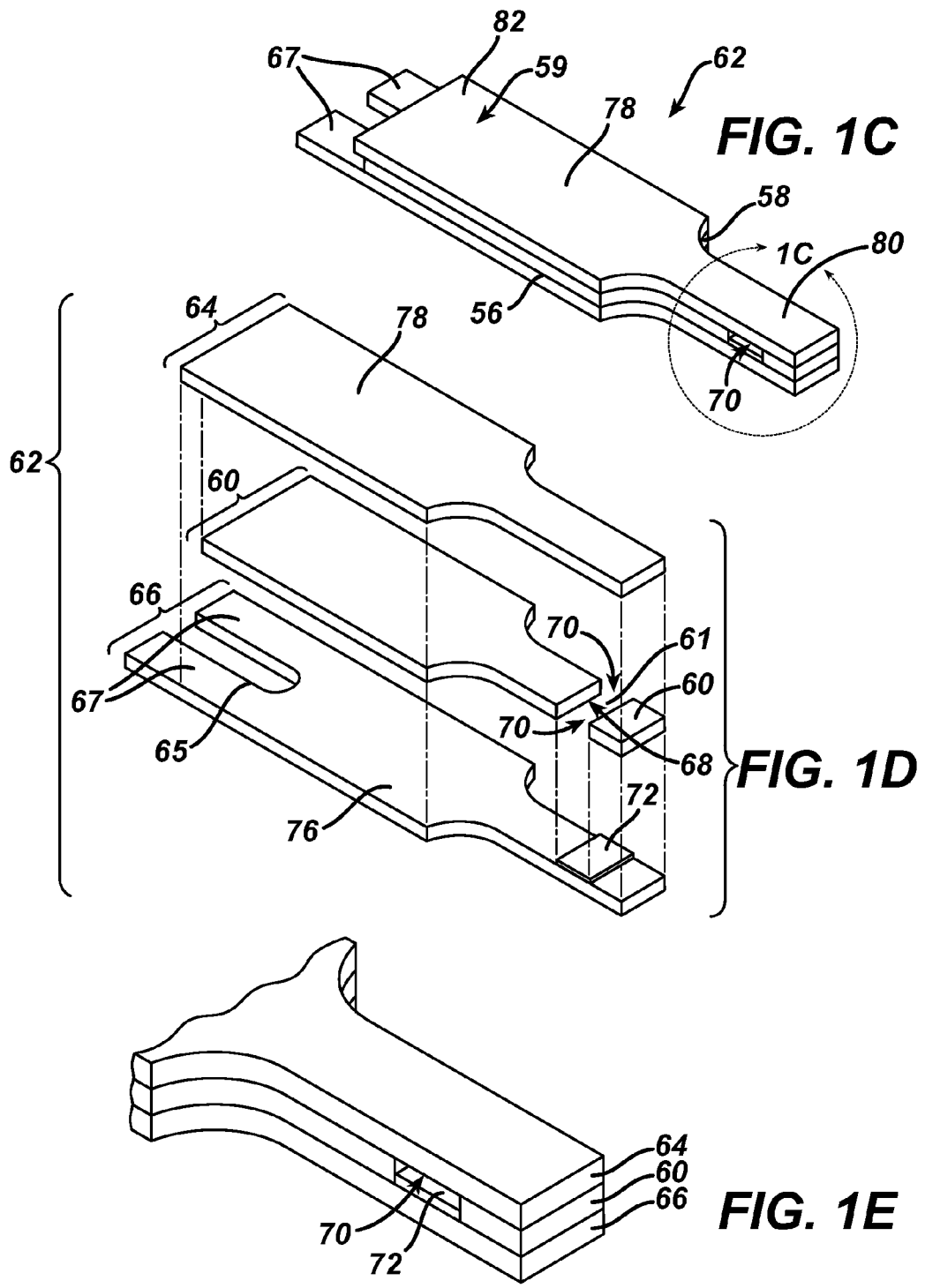

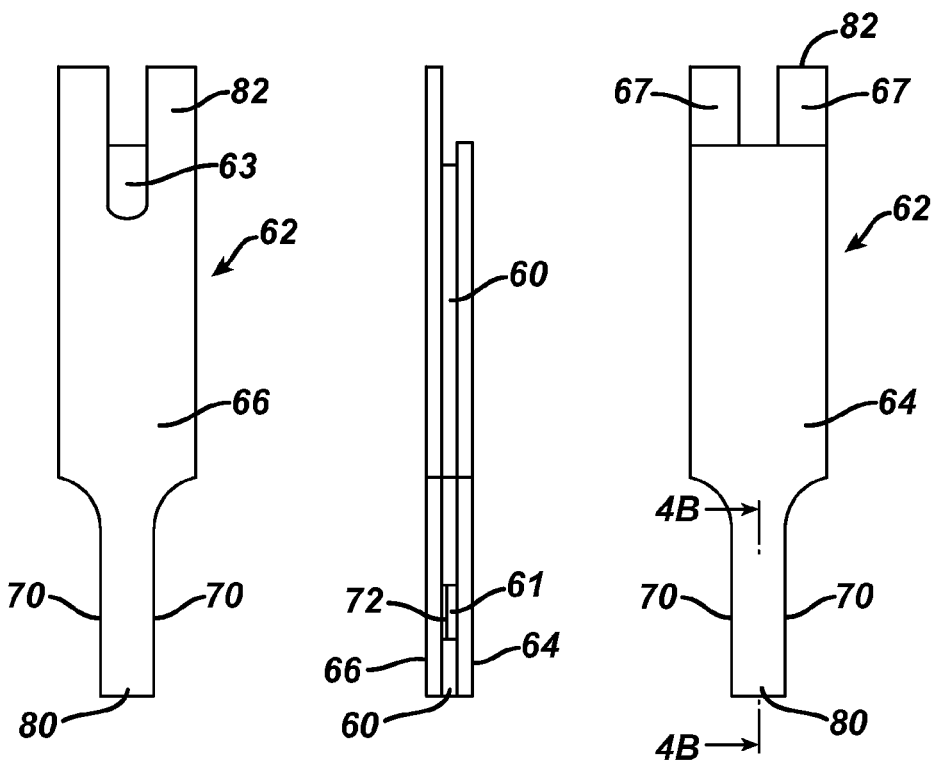
*FIG. 2*  *FIG. 3*  *FIG. 4A*
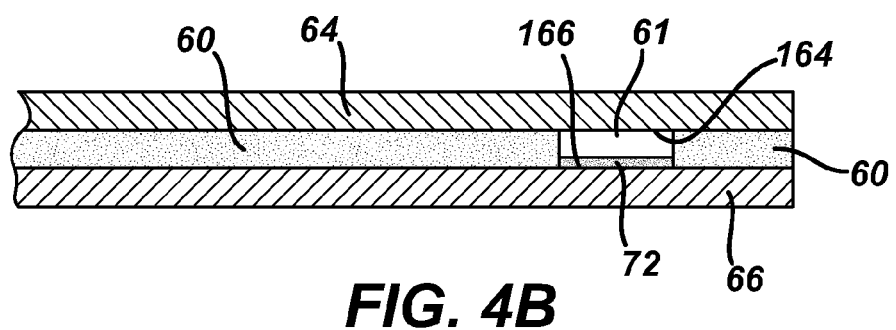
*FIG. 4B*

SYSTEM AND METHOD FOR DETERMINING HEMATOCRIT INSENSITIVE GLUCOSE CONCENTRATION

BACKGROUND

Analyte detection in physiological fluids, e.g. blood or blood derived products, is of ever increasing importance to today's society. Analyte detection assays find use in a variety of applications, including clinical laboratory testing, home testing, etc., where the results of such testing play a prominent role in diagnosis and management in a variety of disease conditions. Analytes of interest include glucose for diabetes management, cholesterol, and the like. In response to this growing importance of analyte detection, a variety of analyte detection protocols and devices for both clinical and home use have been developed.

One type of method that is employed for analyte detection is an electrochemical method. In such methods, an aqueous liquid sample is placed into a sample-receiving chamber in an electrochemical cell that includes two electrodes, e.g., a counter and working electrode. The analyte is allowed to react with a redo reagent to form an oxidizable (or reducible) substance in an amount corresponding to the analyte concentration. The quantity of the oxidizable (or reducible) substance present is then estimated electrochemically and related to the amount of analyte present in the initial sample.

Such systems are susceptible to various modes of inefficiency and/or error. For example, hematocrits or other substances may affect the results of the method.

SUMMARY OF THE DISCLOSURE

Applicant has discovered various techniques to allow a biosensor system to derive precise and accurate glucose concentrations from fluid samples that are generally insensitive to substances such as, for example, hematocrits or any other factors affecting the viscosity of the fluid sample.

In one aspect of this invention, a method of determining blood glucose concentration with a glucose measurement system is provided. The system includes a test strip and test meter. The test meter has a microcontroller configured to apply a plurality of test voltages to the test strip and measure at least a current transient output resulting from an electrochemical reaction in a test chamber of the test strip. The method can be achieved by: inserting the test strip into a strip port connector of the test meter to connect at least two electrodes coupled to the test chamber of the test strip to a strip measurement circuit; initiating a test sequence after deposition of a sample, in which the initiating includes: applying a first voltage of approximately ground potential to the test chamber for a first duration; applying a second voltage to the test chamber for a second duration after the first duration; changing the second voltage to a third voltage different from the second voltage for a third duration after the second duration; switching the third voltage to a fourth voltage different from the third voltage for a fourth duration after the third duration; altering the fourth voltage to a fifth voltage different from the fourth voltage for a fifth duration after the fourth duration; modifying the fifth voltage to a sixth voltage different from the fifth voltage for a sixth duration after the fifth duration; changing the sixth voltage to a seventh voltage different from the sixth voltage for a seventh duration after the sixth duration; measuring at least one of: a first current transient output from the test chamber during a first interval proximate the second and third durations; a second current transient output during a second interval proximate the fourth and fifth durations; a third current transient output during a third interval proximate the fifth and sixth durations; a fourth current transient output during a fourth interval proximate the sixth and seventh durations; and a fifth current transient output during a fifth interval proximate the end of the seventh durations; calculating a glucose concentration of the sample from at least one of the first, second, third, fourth, or fifth current outputs such that bias in the glucose concentration is less than ±10% for glucose concentration(s) less than 75 mg/dL in hematocrits ranging from about 20% to about 60%.

In another aspect of the invention, a method of determining blood glucose concentration with a glucose measurement system is provided in which the system includes a test strip and test meter. The test meter has a microcontroller configured to apply a plurality of test voltages to the test strip and measure at least a current transient output resulting from an electrochemical reaction in a test chamber of the test strip. The method can be achieved by: a inserting the test strip into a strip port connector of the test meter to connect at least two electrodes coupled to the test chamber of the test strip to a strip measurement circuit; initiating a test sequence after deposition of a sample, in which the initiating includes: applying a zero potential for a first duration to the test chamber; driving a plurality of voltages to the test chamber over a plurality of durations after the first duration in which at least one millivolt for one duration is opposite in polarity to another voltage in another duration after the one duration such that the change in polarity produces a plurality of inflections in a current output transient of the test chamber; measuring magnitudes of the current output transient proximate respective inflections of the current transient caused by the change in polarity in the plurality of voltages or proximate an interval during a decay of the current transient; and calculating a glucose concentration of the sample from magnitudes of the current transient of the measuring step.

In a further aspect of the invention, a blood glucose measurement system is provided that includes an analyte test strip and an analyte meter. The analyte test strip includes a substrate having a reagent disposed thereon and at least two electrodes proximate the reagent in a test chamber. The analyte meter includes a strip port connector disposed to connect to the two electrodes, a power supply; and a microcontroller electrically coupled to the strip port connector and the power supply so that, when the test strip is inserted into the strip port connector and a blood sample is deposited in the test chamber for chemical transformations of glucose in the blood sample, a glucose concentration of the blood sample is determined by the microcontroller from at least one of the first, second, third, fourth, or fifth current outputs from the test chamber due to applied voltages such that bias in the glucose concentration is less than ±10% for glucose concentration(s) less than 75 mg/dL in hematocrits ranging from about 20% to about 60%.

In each of the aspects above for the invention, the following features can also be combined in combination with these aspects above to arrive at variations of the invention. For example, in the measurement or sampling of the current at the respective time points, the current measured at each time point may be a summation of current about each time point. To give a few examples, the first current output may be a summation of current outputs from about 0.8 seconds to about 1.1 seconds and preferably from about 0.9 second to about 1 second with respect to initiation of a test sequence voltage; the second current output may be a summation of current outputs from about 2.3 seconds to about 2.6 seconds and preferably from about 2.4 seconds to about 2.5 seconds with respect to initiation of a test sequence voltage; the third current output may be a summation of current outputs from about 3.3 seconds to about 3.6 seconds and preferably from about 3.4 seconds to about 3.5 seconds with respect to initiation of a test sequence voltage; the fourth current output may be a summation of the current outputs from about 3.8 seconds to about 4.1 seconds and preferably from about 3.9 seconds to about 4 seconds with respect to initiation of a test sequence voltage; the fifth current output may be a summation of current outputs from about 4.8 seconds to about 5.1 seconds and preferably from about 4.9 seconds to about 5 seconds with respect to initiation of a test sequence voltage; the second voltage in the system may be a voltage opposite in polarity to the third, fifth and seventh voltages and with the same polarity as the fourth and sixth voltages; each of the second to seventh voltages may be about one millivolt; the calculating may be by utilizing an equation of the form:

$$g = \left(x_1 |I_a|^{\left(x_2 - \frac{x_3}{|I_d|}\right)} \otimes x_4 |I_e| - x_5\right) \Big/ x_6$$

where:
g is glucose concentration;
$I_a$ may be a current output measured proximate an inflection of the output current transient due to a change in applied voltages from the second to the third durations;
$I_d$ may be a current output measured proximate an inflection of the output current transient due to a change in applied voltages from the sixth duration to the seventh duration;
$I_e$ may be a current output measured after the sixth duration but less than 10 seconds after a start of the test sequence;
$x_1$ may be about 203.9;
$x_2$ may be about −0.853;
$x_3$ may be about 20.21;
$x_5$ may be about −100.3; and
$x_6$ may be about 13.04; or alternatively, utilizing an equation of the form:

$$g = \left(\left|\frac{I_b}{I_e}\right|^{\left(x_1 - x_2 \left|\frac{I_d}{I_c}\right|\right)} \otimes x_3 \left|\frac{I_a}{I_d}\right|^{x_4} - x_5\right) \Big/ x_6$$

where:
g is glucose concentration;
$I_a$ may be a current output measured proximate an inflection of the output current transient due to a change in applied voltages from the second to the third durations;
$I_b$ may be a current output measured proximate an inflection of the output current transient due to a change in applied voltages from the fourth duration to the fifth duration;
$I_c$ may be a current output measured proximate an inflection of the output current transient due to a change in applied voltages from the fifth duration to the sixth duration;
$I_d$ may be a current output measured proximate an inflection of the output current transient due to a change in applied voltages from the sixth duration to the seventh duration;
$I_e$ may be a current output measured after the sixth duration but less than 10 seconds after a start of the test sequence;

$x_1$ may be about −1.114;
$x_2$ may be about −1.930;
$x_3$ may be about 74.23;
$x_4$ may be about −1.449;
$x_5$ may be about 275.0; and
$x_6$ may be about 7.451; in addition, the calculating may be by utilizing an equation of the form:

$$g = \left(\left|\frac{I_b}{I_a}\right|^{\left(x_1 - x_2 \left|\frac{I_d}{I_e}\right|\right)} \otimes x_3 I_c - x_4\right) \Big/ x_5$$

Where:
g is glucose concentration;
$I_a$ may be a current output measured proximate an inflection of the output current transient due to a change in applied voltages from the second to the third durations;
$I_b$ may be a current output measured proximate an inflection of the output current transient due to a change in applied voltages from the fourth duration to the fifth duration;
$I_c$ may be a current output measured proximate an inflection of the output current transient due to a change in applied voltages from the fifth duration to the sixth duration;
$I_d$ may be a current output measured proximate an inflection of the output current transient due to a change in applied voltages from the sixth duration to the seventh duration;
$I_e$ may be a current output measured after the sixth duration but less than 10 seconds after a start of the test sequence;
$x_1$ may be about 1.190;
$x_2$ may be about 1.280;
$x_3$ may be about 5.905;
$x_4$ may be about 53.01;
$x_5$ may be about 2.473.

Further, the calculating may be by utilizing an equation of the form:

$$g = x_1 \log\left(x_2 \left|\frac{I_c}{I_b}\right|\right) \otimes |I_e| + x_3$$

where:
g is glucose concentration;
$I_b$ may be a current output measured proximate an inflection of the output current transient due to a change in applied voltages from the fourth duration to the fifth duration;
$I_c$ may be a current output measured proximate an inflection of the output current transient due to a change in applied voltages from the fifth duration to the sixth duration;
$I_e$ may be a current output measured after the sixth duration but less than 10 seconds after a start of the test sequence;
$x_1$ may be about 1.569;
$x_2$ may be about 2.080; and
$x_3$ may be about −2.661;

alternatively, the calculating may be by utilizing an equation of the form:

$$g = \left|\frac{I_d}{I_a}\right|^{x_1} \otimes \left|\frac{|I_e| + x_4|I_a| - 2|I_b|}{|I_e| + x_4|I_a|}\right| \otimes I_e \left| \otimes x_2/x_3 \right.$$

where:
- g is glucose concentration;
- $I_a$ may be a current output measured proximate an inflection of the output current transient due to a change in applied voltages from the second to the third durations;
- $I_b$ may be a current output measured proximate an inflection of the output current transient due to a change in applied voltages from the fourth duration to the fifth duration;
- $I_d$ may be a current output measured proximate an inflection of the output current transient due to a change in applied voltages from the sixth duration to the seventh duration;
- $I_e$ may be a current output measured after the sixth duration but less than 10 seconds after a start of the test sequence;
- $x_1$ may be about 1.580;
- $x_2$ may be about 0.142;
- $x_3$ may be about 3.260; and
- $x_4$ may be about 46.40.

These and other embodiments, features and advantages will become apparent to those skilled in the art when taken with reference to the following more detailed description of various exemplary embodiments of the invention in conjunction with the accompanying drawings that are first briefly described.

BRIEF DESCRIPTION OF THE DRAWINGS

The accompanying drawings, which are incorporated herein and constitute part of this specification, illustrate presently preferred embodiments of the invention, and, together with the general description given above and the detailed description given below, serve to explain features of the invention (wherein like numerals represent like elements).

FIG. 1C illustrates a perspective view of an assembled test strip suitable for use in the system and methods disclosed herein;

FIG. 1D illustrates an exploded perspective view of an unassembled test strip suitable for use in the system and methods disclosed herein;

FIG. 1E illustrates an expanded perspective view of a proximal portion of the test strip suitable for use in the system and methods disclosed herein;

FIG. 2 is a bottom plan view of one embodiment of a test strip disclosed herein;

FIG. 3 is a side plan view of the test strip of FIG. 2;

FIG. 4A is a top plan view of the test strip of FIG. 3;

FIG. 4B is a partial side view of a proximal portion of the test strip of FIG. 4A;

MODES FOR CARRYING OUT THE INVENTION

The following detailed description should be read with reference to the drawings, in which like elements in different drawings are identically numbered. The drawings, which are not necessarily to scale, depict selected embodiments and are not intended to limit the scope of the invention. The detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention.

As used herein, the terms "about" or "approximately" for any numerical values or ranges indicate a suitable dimensional tolerance that allows the part or collection of components to function for its intended purpose as described herein. In addition, as used herein, the terms "patient," "host," "user," and "subject" refer to any human or animal subject and are not intended to limit the systems or methods to human use, although use of the subject invention in a human patient represents a preferred embodiment.

Figure 1A:
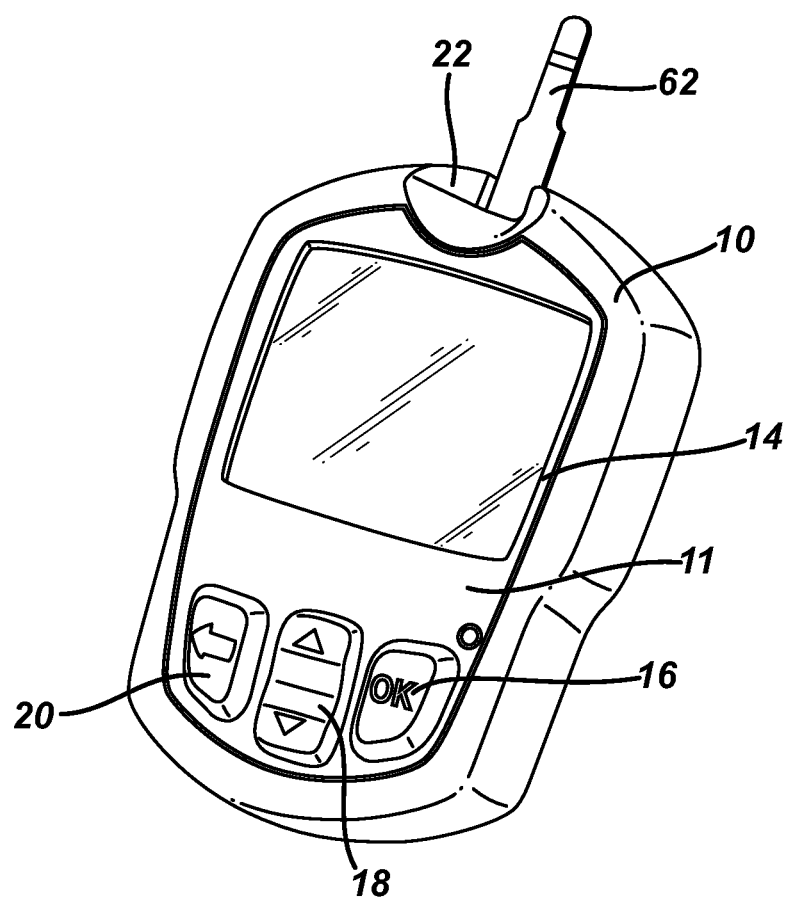
FIG. 1A illustrates a preferred blood glucose measurement system.

FIG. 1A illustrates a diabetes management system that includes a meter 10 and a biosensor in the form of a glucose test strip 62. Note that the meter (meter unit) may be referred to as an analyte measurement and management unit, a glucose meter, a meter, and an analyte measurement device. In an embodiment, the meter unit may be combined with an insulin delivery device, an additional analyte testing device, and a drug delivery device. The meter unit may be connected to a remote computer or remote server via a cable or a suitable wireless technology such as, for example, GSM, CDMA, BlueTooth, WiFi and the like.

Referring back to FIG. 1A, glucose meter or meter unit 10 may include a housing 11, user interface buttons (16, 18, and 20), a display 14, and a strip port opening 22. User interface buttons (16, 18, and 20) may be configured to allow the entry of data, navigation of menus, and execution of commands. User interface button 18 may be in the form of a two way toggle switch. Data may include values representative of analyte concentration, and/or information, which are related to the everyday lifestyle of an individual. Information, which is related to the everyday lifestyle, may include food intake, medication use, occurrence of health check-ups, and general health condition and exercise levels of an individual. The electronic components of meter 10 may be disposed on a circuit board 34 that is within housing 11.

Figure 1B:
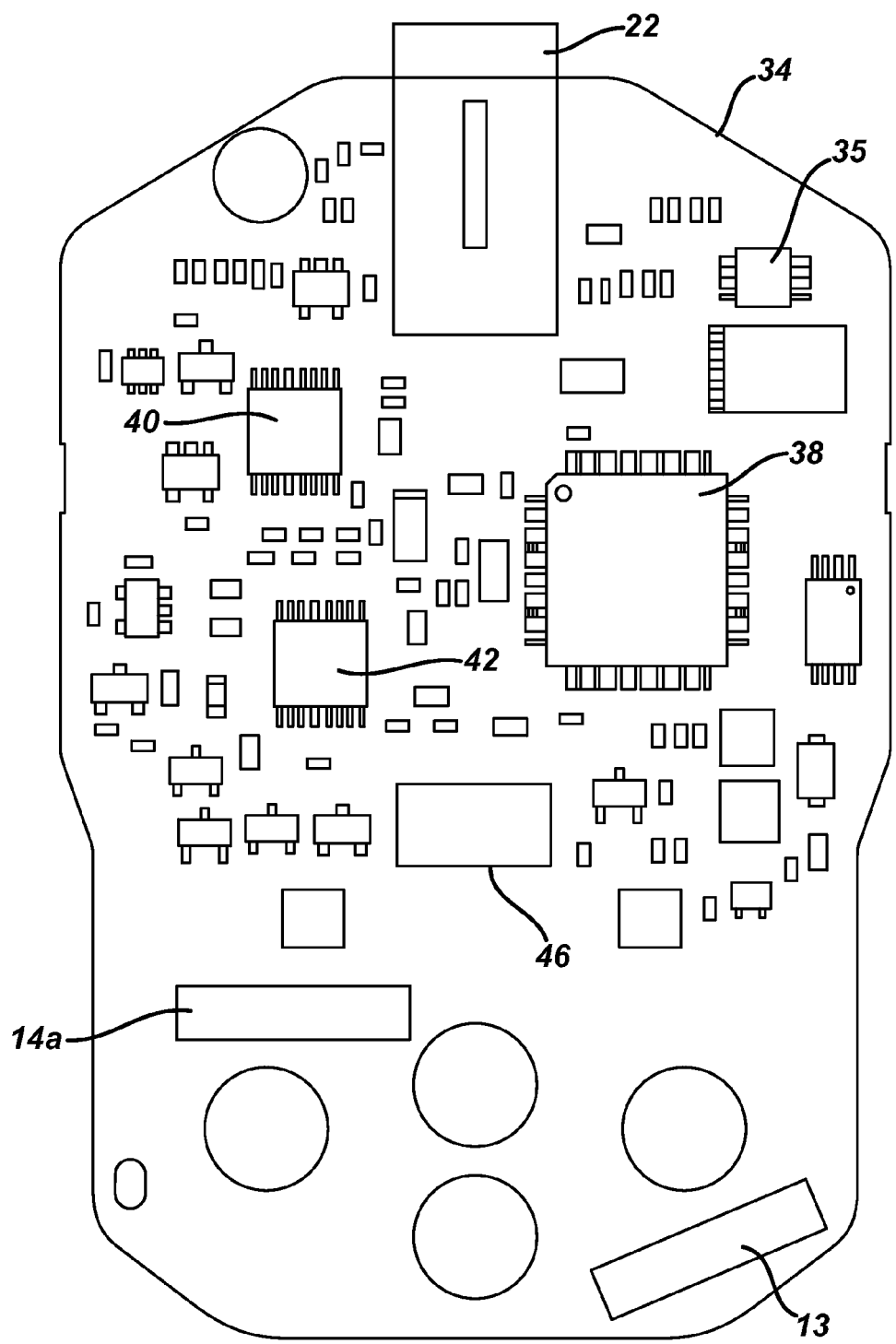
FIG. 1B illustrates the various components disposed in the meter of FIG. 1A.

FIG. 1B illustrates (in simplified schematic form) the electronic components disposed on a top surface of circuit board 34. On the top surface, the electronic components include a strip port connector 22, an operational amplifier circuit 35, a microcontroller 38, a display connector 14a, a non-volatile memory 40, a clock 42, and a first wireless module 46. On the bottom surface, the electronic components may include a battery connector (not shown) and a data port 13. Microcontroller 38 may be electrically connected to strip port connector 22, operational amplifier circuit 35, first wireless module 46, display 14, non-volatile memory 40, clock 42, battery, data port 13, and user interface buttons (16, 18, and 20).

Operational amplifier circuit 35 may include two or more operational amplifiers configured to provide a portion of the potentiostat function and the current measurement function. The potentiostat function may refer to the application of a test voltage between at least two electrodes of a test strip. The current function may refer to the measurement of a test current resulting from the applied test voltage. The current measurement may be performed with a current-to-voltage converter. Microcontroller 38 may be in the form of a mixed signal microprocessor (MSP) such as, for example, the Texas Instrument MSP 430. The TI-MSP 430 may be configured to also perform a portion of the potentiostat function and the current measurement function. In addition, the MSP 430 may also include volatile and non-volatile memory. In another embodiment, many of the electronic components may be integrated with the microcontroller in the form of an application specific integrated circuit (ASIC).

Strip port connector 22 may be configured to form an electrical connection to the test strip. Display connector 14a may be configured to attach to display 14. Display 14 may be in the form of a liquid crystal display for reporting measured glucose levels, and for facilitating entry of lifestyle related information. Display 14 may optionally include a backlight. Data port 13 may accept a suitable connector attached to a connecting lead, thereby allowing glucose meter 10 to be linked to an external device such as a personal computer. Data port 13 may be any port that allows for transmission of data such as, for example, a serial, USB, or a parallel port. Clock 42 may be configured to keep current time related to the geographic region in which the user is located and also for measuring time. The meter unit may be configured to be electrically connected to a power supply such as, for example, a battery.

FIGS. 1C-1E, 2, 3, and 4B show various views of an exemplary test strip 62 suitable for use with the methods and systems described herein. In an exemplary embodiment, a test strip 62 is provided which includes an elongate body extending from a distal end 80 to a proximal end 82, and having lateral edges 56, 58, as illustrated in FIG. 1C. As shown in FIG. 1D, the test strip 62 also includes a first electrode layer 66, a second electrode layer 64, and a spacer 60 sandwiched in between the two electrode layers 64 and 66. The first electrode layer 66 may include a first electrode 66, a first connection track 76, and a first contact pad 67, where the first connection track 76 electrically connects the first electrode 66 to the first contact pad 67, as shown in FIGS. 1D and 4B. Note that the first electrode 66 is a portion of the first electrode layer 66 that is immediately underneath the reagent layer 72, as indicated by FIGS. 1D and 4B. Similarly, the second electrode layer 64 may include a second electrode 64, a second connection track 78, and a second contact pad 63, where the second connection track 78 electrically connects the second electrode 64 with the second contact pad 63, as shown in FIGS. 1D, 2, and 4B. Note that the second electrode 64 is a portion of the second electrode layer 64 that is above the reagent layer 72, as indicated by FIG. 4B.

As shown, the sample-receiving chamber 61 is defined by the first electrode 66, the second electrode 64, and the spacer 60 near the distal end 80 of the test strip 62, as shown in FIGS. 1D and 4B. The first electrode 66 and the second electrode 64 may define the bottom and the top of sample-receiving chamber 61, respectively, as illustrated in FIG. 4B. A cutout area 68 of the spacer 60 may define the sidewalls of the sample-receiving chamber 61 along with upper wall 164 and lower wall 166, as illustrated in FIG. 4B. In one aspect, the sample-receiving chamber 61 may include ports 70 that provide a sample inlet and/or a vent, as shown in FIGS. 1C to 1E. For example, one of the ports may allow a fluid sample to ingress and the other port may allow air to egress.

In an exemplary embodiment, the sample-receiving chamber 61 (or test cell or test chamber) may have a small volume. For example, the chamber 61 may have a volume in the range of from about 0.1 microliters to about 5 microliters, about 0.2 microliters to about 3 microliters, or, preferably, about 0.3 microliters to about 1 microliter. To provide the small sample volume, the cutout 68 may have an area ranging from about 0.01 $cm^2$ to about 0.2 $cm^2$, about 0.02 $cm^2$ to about 0.15 $cm^2$, or, preferably, about 0.03 $cm^2$ to about 0.08 $cm^2$. In addition, first electrode 66 and second electrode 64 may be spaced apart in the range of about 1 micron to about 500 microns, preferably between about 10 microns and about 400 microns, and more preferably between about 40 microns and about 200 microns. The relatively close spacing of the electrodes may also allow redox cycling to occur, where oxidized mediator generated at first electrode 66, may diffuse to second electrode 64 to become reduced, and subsequently diffuse back to first electrode 66 to become oxidized again. Those skilled in the art will appreciate that various such volumes, areas, and/or spacing of electrodes is within the spirit and scope of the present disclosure.

In one embodiment, the first electrode layer 66 and the second electrode layer 64 may be a conductive material formed from materials such as gold, palladium, carbon, silver, platinum, tin oxide, iridium, indium, or combinations thereof (e.g., indium doped tin oxide). In addition, the electrodes may be formed by disposing a conductive material onto an insulating sheet (not shown) by a sputtering, electroless plating, or a screen-printing process. In one exemplary embodiment, the first electrode layer 66 and the second electrode layer 64 may be made from sputtered palladium and sputtered gold, respectively. Suitable materials that may be employed as spacer 60 include a variety of insulating materials, such as, for example, plastics (e.g., PET, PETG, polyimide, polycarbonate, polystyrene), silicon, ceramic, glass, adhesives, and combinations thereof. In one embodiment, the spacer 60 may be in the form of a double sided adhesive coated on opposing sides of a polyester sheet where the adhesive may be pressure sensitive or heat activated. Applicants note that various other materials for the first electrode layer 66, the second electrode layer 64, and/or the spacer 60 are within the spirit and scope of the present disclosure.

Either the first electrode 66 or the second electrode 64 may perform the function of a working electrode depending on the magnitude and/or polarity of the applied test voltage. The working electrode may measure a limiting test current that is proportional to the reduced mediator concentration. For example, if the current limiting species is a reduced mediator (e.g., ferrocyanide), then it may be oxidized at the first electrode 66 as long as the test voltage is sufficiently greater than the redox mediator potential with respect to the second electrode 64. In such a situation, the first electrode 66 performs the function of the working electrode and the second electrode 64 performs the function of a counter/reference electrode. Applicants note that one may refer to a counter/reference electrode simply as a reference electrode or a counter electrode. A limiting oxidation occurs when all reduced mediator has been depleted at the working electrode surface such that the measured oxidation current is proportional to the flux of reduced mediator diffusing from the bulk solution towards the working electrode surface. The term "bulk solution" refers to a portion of the solution sufficiently far away from the working electrode where the reduced mediator is not located within a depletion zone. It should be noted that unless otherwise stated for test strip 62, all potentials applied by test meter 10 will hereinafter be stated with respect to second electrode 64.

Similarly, if the test voltage is sufficiently less than the redox mediator potential, then the reduced mediator may be oxidized at the second electrode 64 as a limiting current. In such a situation, the second electrode 64 performs the function of the working electrode and the first electrode 66 performs the function of the counter/reference electrode.

Initially, an analysis may include introducing a quantity of a fluid sample into a sample-receiving chamber 61 via a port 70. In one aspect, the port 70 and/or the sample-receiving chamber 61 may be configured such that capillary action causes the fluid sample to fill the sample-receiving chamber 61. The first electrode 66 and/or second electrode 64 may be coated with a hydrophilic reagent to promote the capillarity of the sample-receiving chamber 61. For example, thiol derivatized reagents having a hydrophilic moiety such as 2-mercaptoethane sulfonic acid may be coated onto the first electrode and/or the second electrode.

In the analysis of strip 62 above, reagent layer 72 can include glucose dehydrogenase (GDH) based on the PQQ co-factor and ferricyanide. In another embodiment, the enzyme GDH based on the PQQ co-factor may be replaced with the enzyme GDH based on the FAD co-factor. When blood or control solution is dosed into a sample reaction chamber 61, glucose is oxidized by $GDH_{(ox)}$ and in the process converts $GDH_{(ox)}$ to $GDH_{(red)}$ as shown in the chemical transformation T.1 below. Note that $GDH_{(ox)}$ refers to the oxidized state of GDH, and $GDH_{(red)}$ refers to the reduced state of GDH.

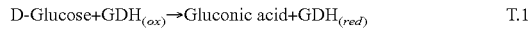

$$\text{D-Glucose} + GDH_{(ox)} \rightarrow \text{Gluconic acid} + GDH_{(red)} \qquad \text{T.1}$$

Next, $GDH_{(red)}$ is regenerated back to its active oxidized state by ferricyanide (i.e. oxidized mediator or $Fe(CN)_6^{3-}$) as shown in chemical transformation T.2 below. In the process of regenerating $GDH_{(ox)}$, ferrocyanide (i.e. reduced mediator or $Fe(CN)_6^{4-}$) is generated from the reaction as shown in T.2:

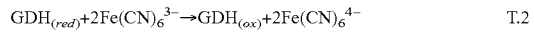

$$GDH_{(red)} + 2Fe(CN)_6^{3-} \rightarrow GDH_{(ox)} + 2Fe(CN)_6^{4-} \qquad \text{T.2}$$

Figure 5:
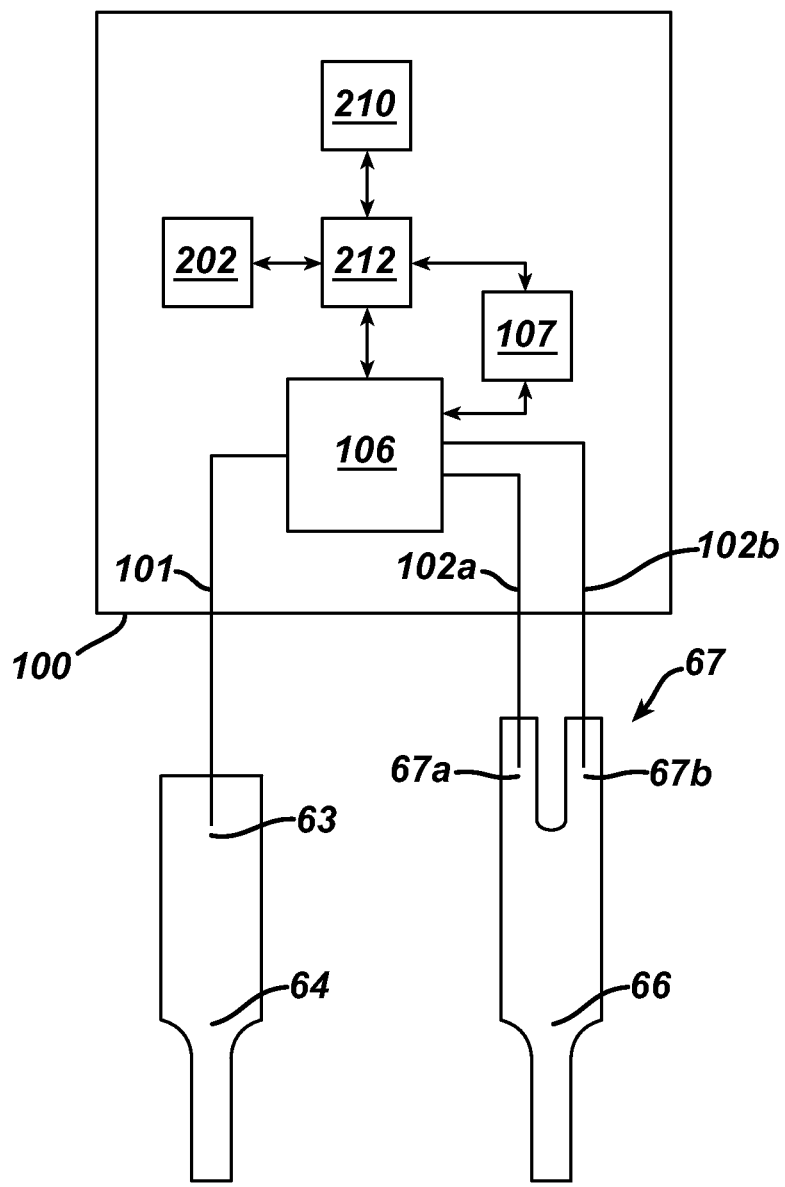
FIG. 5 is a simplified schematic showing a test meter electrically interfacing with portions of a test strip disclosed herein.

FIG. 5 provides a simplified schematic showing a test meter 100 interfacing with a first contact pad 67a, 67b and a second contact pad 63. The second contact pad 63 may be used to establish an electrical connection to the test meter through a U-shaped notch 65, as illustrated in FIGS. 1D and 2. In one embodiment, the test meter 100 may include a second electrode connector 101, and first electrode connectors (102a, 102b), a test voltage unit 106, a current measurement unit 107, a processor 212, a memory unit 210, and a visual display 202, as shown in FIG. 5. The first contact pad 67 may include two prongs denoted as 67a and 67b. In one exemplary embodiment, the first electrode connectors 102a and 102b separately connect to prongs 67a and 67b, respectively. The second electrode connector 101 may connect to second contact pad 63. The test meter 100 may measure the resistance or electrical continuity between the prongs 67a and 67b to determine whether the test strip 62 is electrically connected to the test meter 10.

In one embodiment, the test meter 100 may apply a test voltage and/or a current between the first contact pad 67 and the second contact pad 63. Once the test meter 100 recognizes that the strip 62 has been inserted, the test meter 100 turns on and initiates a fluid detection mode. In one embodiment, the fluid detection mode causes test meter 100 to apply a constant current of about 1 microampere between the first electrode 66 and the second electrode 64. Because the test strip 62 is initially dry, the test meter 10 measures a relatively large voltage. When the fluid sample bridges the gap between the first electrode 66 and the second electrode 64 during the dosing process, the test meter 100 will measure a decrease in measured voltage that is below a predetermined threshold causing test meter 10 to automatically initiate the glucose test.

Applicant has determined that in order to extract accurate as well as precise glucose concentration value, the waveform or driving voltage must be tailored so as to produce a stable current transient output from the biosensor. This is particularly important since the repeatability of points in the transients correlated to glucose concentration must be as high as possible. Also, by providing such current transient, it allows applicant to obtained several independent techniques to calculate a glucose concentration value that are virtually insensitive to hematocrits in blood samples.

Figure 6A:
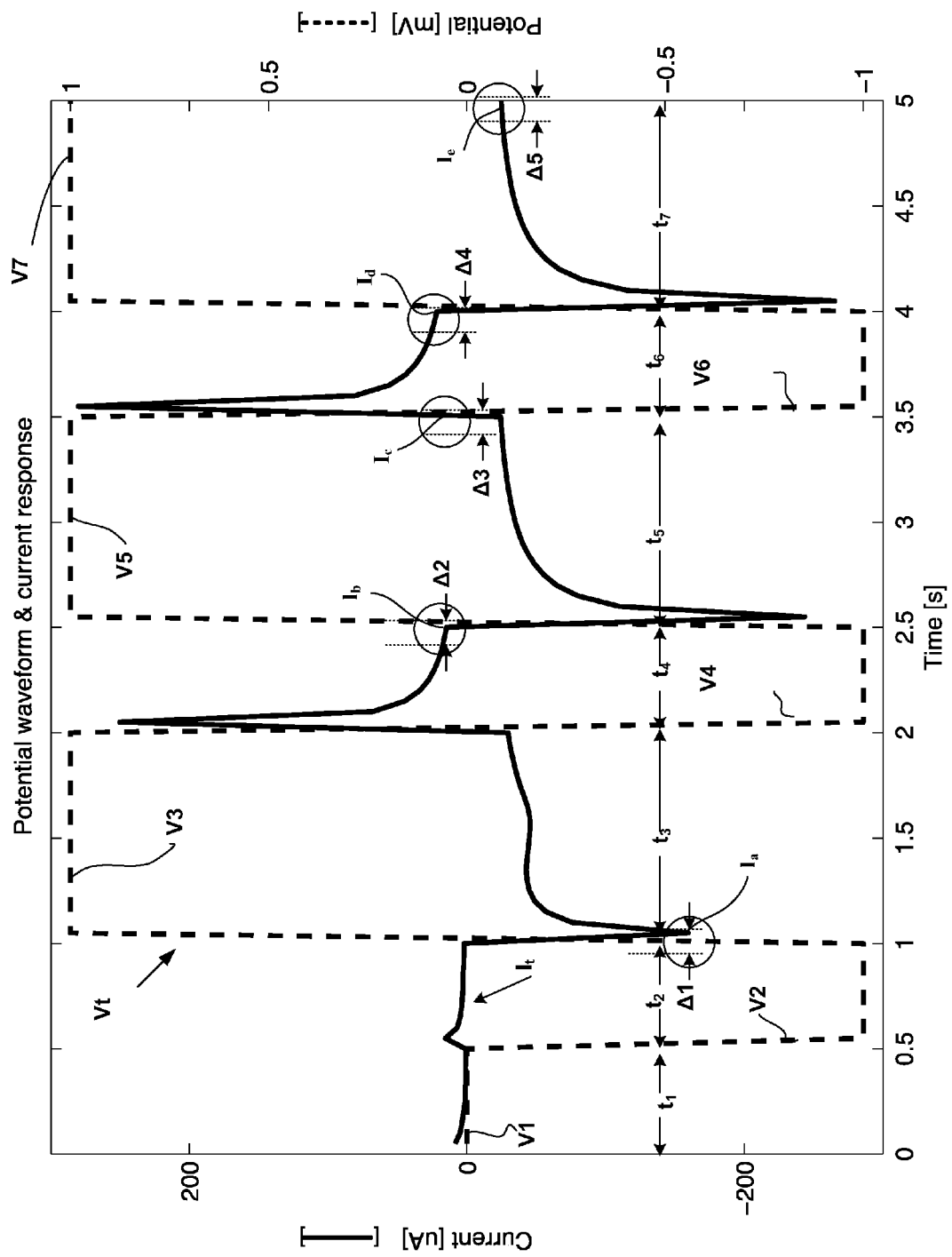
FIG. 6A is a graph of a input potential applied to the biosensor and output current from the biosensor during a test sequence.
Figure 6B:
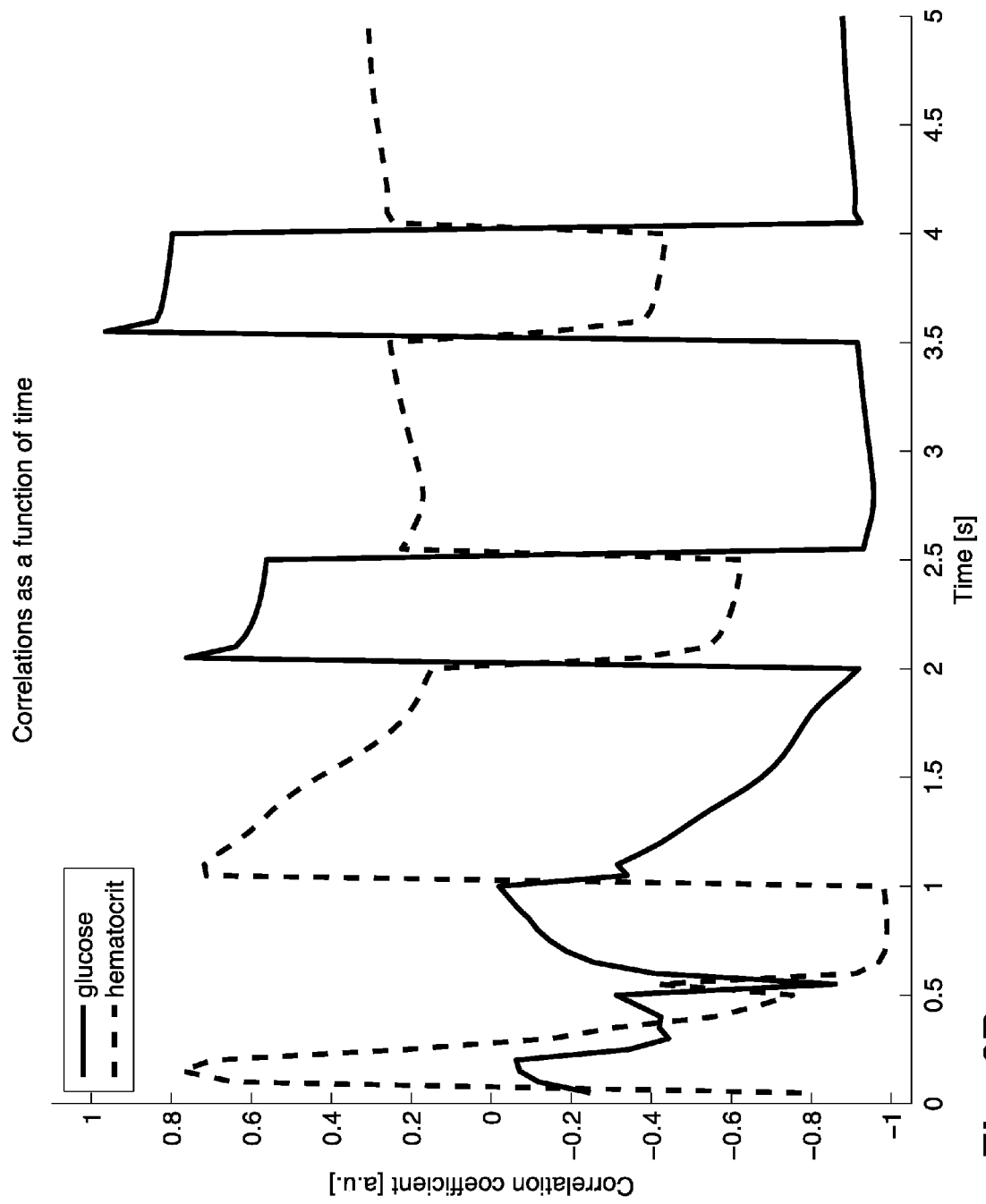
FIG. 6B is a graph showing correlations between current and glucose (solid line) as well as current and hematocrit (dashed line) as a function of time.

FIG. 6A illustrates a particular waveform (dashed line labeled "Vt") deemed suitable for applicant's objective with this particular biosensor and the resulting current transient (solid line labeled as "$I_t$"). FIG. 6B provides an insight into where the correlations (vertical axis) lie within the current transient towards glucose as well as hematocrit. One will observe that generally there are regions within the current response (i.e. transient), which exhibit different sensitivities to measured analyte (glucose) as well as the inherent interference (here: hematocrit). This shapes the derivation of the applicant's technique. In particular, applicant has devised each technique so that results from hematocrit sensitive regions of the transient can be used to correct for the glucose result obtained using glucose sensitive regions. One will note that there is no single point within the current transient, which doesn't correlate to hematocrit, but at the same time gives maximum glucose correlation. Hence, each technique tries to artificially create such conditions. The overriding idea was to use only stable points within the current output transient, i.e. sampling points were chosen as far as possible away from the peaks. Here the distance from the peak to the sampling point to the right of the peak is important, as what comes after the sampling point has no bearing on the sampling point's stability and reproducibility.

In devising the appropriate technique, applicant initially utilized the waveform Vt to obtain current transient $I_t$ of FIG. 6A along with Equation A, which is of the form:

$$g = \frac{|I_e| - x_2}{x_1}. \qquad \text{Equation A}$$

where

"g" is the glucose concentration, $I_e$ may be a current output measured proximate at the end of the measurement (e.g., about 4.9-5 seconds with respect to initiation of the measuring sequence);

$x_1$=0.427, and $x_2$=25.62.

Figure 8:
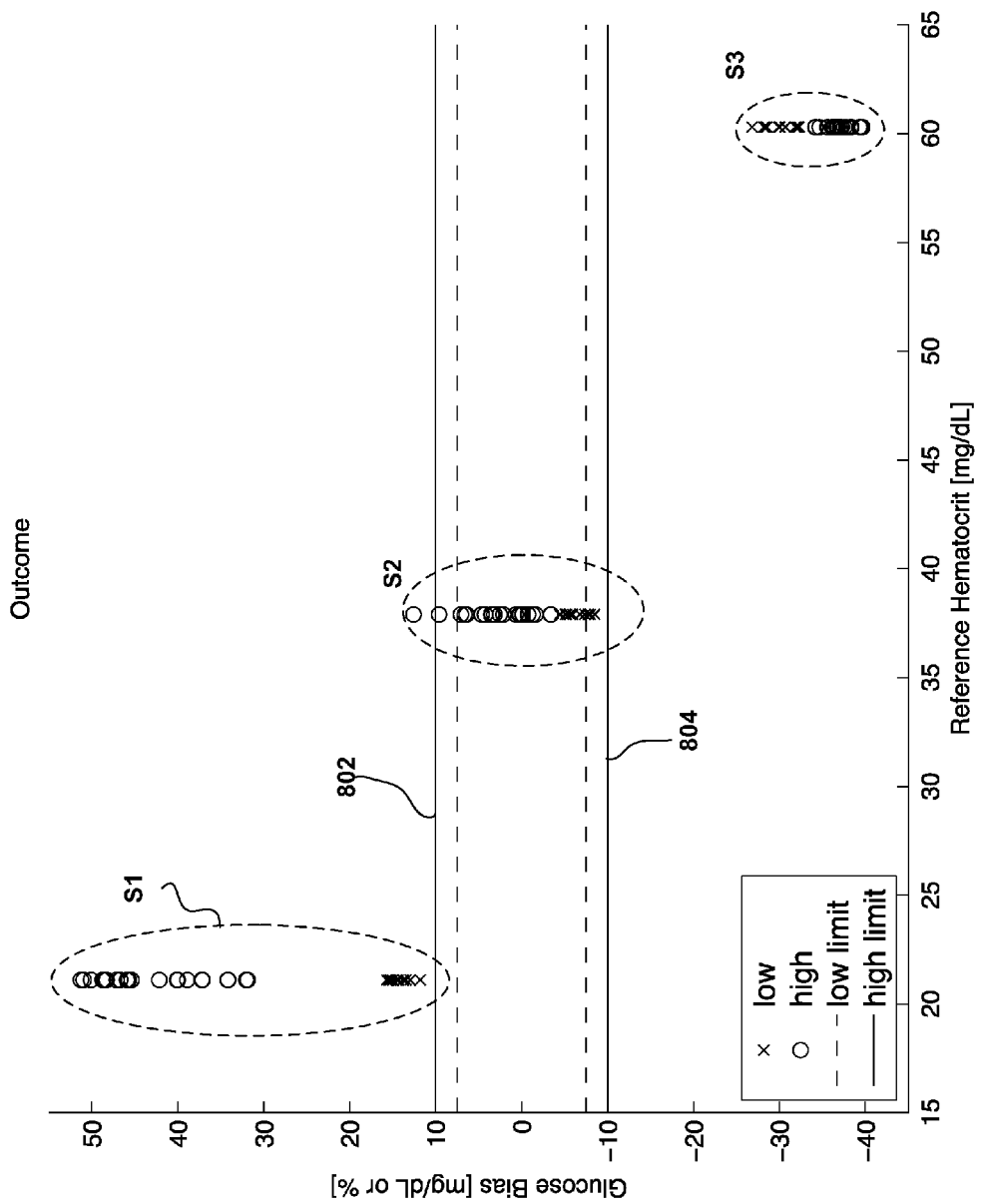
FIG. 8 illustrates bias or errors for three samples S1, S2, S3 (with different levels of hematocrits) as compared to referential glucose values when an initial attempt was devised to calculate glucose concentration.

However, when tests were conducted to validate the results of applicant's first attempt (using Equation A), it was discovered, as shown in FIG. 8, that the glucose concentrations were greatly affected when there were low hematocrits (20%) and high hematocrits (60%). Specifically, in FIG. 8, 106 samples S1, S2, S3 of varying glucose concentrations (75 mg/dL or greater and less than 75 mg/dL) within three different hematocrits (20%, 38%, and 60%) were tested and benchmarked against referential (or actual) analyte level (e.g., blood glucose concentration) using a standard laboratory analyzer such as Yellow Springs Instrument (YSI). The bias for glucose concentration "g" and corrected glucose concentration was determined with equations of the form:

$$Bias_{abs} = G_{calculated} - G_{reference} \qquad \text{Equation B}$$

for $G_{reference}$ less than 75 mg/dL glucose with a bias target of 15 mg/dL or 20%.

$$Bias_{\%} = \left(\frac{G_{calculated} - G_{reference}}{G_{reference}}\right) * 100 \qquad \text{Equation C}$$

for $G_{reference}$ greater than or equal to 75 mg/dL glucose with a bias target of 15 mg/dL or 10%.

where:

$Bias_{abs}$ is absolute bias, $Bias_{\%}$ is percent bias, $G_{calculated}$ is the uncorrected or corrected glucose concentration "g" and $G_{reference}$ is the reference glucose concentration.

Referring back to FIG. 8, it can be seen that the glucose concentrations at 20% and 60% hematocrits were believed to be severely impacted by the presence of hematocrits such that measurements in sample S1(at 20% hematocrit) and in sample S3(at 60% hematocrit) were outside of preferred upper limit 802 and lower limit 804. While the performance with this initial technique might be sufficient, nevertheless, it is believed that where samples containing very low (e.g., 20%) or very high (e.g., 60%) hematocrits were utilized, the initial technique of Equation A may not provide a desired performance.

Applicant, however, was able to devise various techniques, which allowed the system to overcome this less than desired performance with the initial technique using Equation A. In particular, with reference to FIG. 7, a method 700 of determining glucose concentration with the biosensor of FIG. 1 will now be described. At step 702, the method may begin with the user inserting the test strip into a strip port connector of the test meter to connect at least two electrodes coupled to the test chamber of the test strip to a strip measurement circuit. At step 704, the user deposit an appropriate sample (e.g., physiological fluid, blood or control solution) onto the test chamber thereby initiating a test sequence after deposition of a sample at step 706. Step 706, (with reference to FIG. 6A) includes many sub-steps involved in the test sequence such as, for example, applying a zero potential V1 for a first duration $t_1$ to the test chamber; driving a plurality of voltages (e.g., V2, V3, V4, V5, V6, and V7) to the test chamber over a plurality of durations ($t_2$, $t_3$, $t_4$, $t_5$, $t_6$, and $t_7$ in FIG. 6A) after the first duration $t_1$ in which at least one millivolt (e.g., V2 in FIG. 6A) for one duration (e.g., $t_2$ in FIG. 6A) is opposite in polarity to another voltage (e.g., V3 in FIG. 6A) in another duration (e.g., $t_3$) after the one duration (i.e., $t_2$ in FIG. 6A) such that the change in polarity produces an inflection (e.g., $I_a$) in a current output transient It of the test chamber. At step 708, which could be conducted in parallel or concurrently with the sub-steps of step 706 such as, for example, measuring magnitudes (e.g., $I_a$, $I_b$, $I_c$, $I_c$, and $I_e$ in FIG. 6A) of the current output transient $I_t$ proximate respective inflections of the current transient caused by the change in polarity in the plurality of voltages or a current magnitude $I_e$ proximate an interval $\Delta 5$ in a decay of the current transient $I_t$. Although it is preferred that the current magnitude be sampled at specific time point, in practice the current magnitude is measured over a very short interval (e.g., $\Delta 1 \ldots \Delta 4$ in FIG. 6A) during the inflection of the current transient $I_t$ and for a predetermined interval $\Delta 5$ at a predetermined time point on the decay of the current transient $I_t$. In the preferred embodiments, the intervals $\Delta 1 \ldots \Delta 4$ may have generally the same sampling time interval. Alternatively, the sampling time intervals $\Delta 1 \ldots \Delta 5$ may have different sampling time intervals. As can be seen in FIG. 6A, the second, fourth, or sixth duration is about ½ second whereas the third, fifth or seventh duration is about one second. Alternatively, the time interval for each duration $t_1$, $t_2$, $t_3$, $t_4$, $t_5$, $t_6$, and $t_7$ can be of the same duration.

At step 710, the logic proceeds by calculating a glucose concentration of the sample from magnitudes ($I_a$, $I_b$, $I_e$, $I_e$, and $I_e$ in FIG. 6A) of the current transient $I_t$ of the measuring step. For example, the glucose calculation can be performed with Equation 1 of the following form:

$$g = \left(x_1 |I_a|^{\left(x_2 - \frac{x_3}{|I_d|}\right)} \otimes x_4 |I_e| - x_5\right) / x_6 \qquad \text{Equation 1}$$

where:

g is glucose concentration;

$I_a$ may be a current output measured proximate an inflection of the output current transient due to a change in applied voltages from the second to the third durations;

$I_d$ may be a current output measured proximate an inflection of the output current transient due to a change in applied voltages from the sixth duration to the seventh duration;

$I_e$ may be a current output measured after the sixth duration but less than 10 seconds after a start of the test sequence;

$x_1$ may be about 203.9;

$x_2$ may be about −0.853;

$x_3$ may be about 20.21;

$x_5$ may be about −100.3; and $x_6$ may be about 13.04.

Alternatively, the glucose calculation can be performed with Equation 2 of the following form:

$$g = \left( \left| \frac{I_b}{I_e} \right|^{(x_1 - x_2 |\frac{I_d}{I_c}|)} \otimes x_3 \left| \frac{I_a}{I_d} \right|^{x_4} - x_5 \right) / x_6.$$ Equation 2 where:
- g is glucose concentration;
- $I_a$ may be a current output measured proximate an inflection of the output current transient due to a change in applied voltages from the second to the third durations;
- $I_b$ may be a current output measured proximate an inflection of the output current transient due to a change in applied voltages from the fourth duration to the fifth duration
- $I_c$ may be a current output measured proximate an inflection of the output current transient due to a change in applied voltages from the fifth duration to the sixth duration;
- $I_d$ may be a current output measured proximate an inflection of the output current transient due to a change in applied voltages from the sixth duration to the seventh duration;
- $I_e$ may be a current output measured after the sixth duration but less than 10 seconds after a start of the test sequence;
- $x_1$ may be about −1.114;
- $x_2$ may be about −1.930;
- $x_3$ may be about 74.23;
- $x_4$ may be about −1.449;
- $x_5$ may be about 275.0; and
- $x_6$ may be about 7.451.

In yet a further variation, the glucose calculation can be performed with Equation 3 of the following form:

$$g = \left( \left| \frac{I_b}{I_a} \right|^{(x_1 - x_2 |\frac{I_d}{I_e}|)} \otimes x_3 I_c - x_4 \right) / x_5$$ Equation 3

Where:
- g is glucose concentration;
- $I_a$ may be a current output measured proximate an inflection of the output current transient due to a change in applied voltages from the second to the third durations;
- $I_b$ may be a current output measured proximate an inflection of the output current transient due to a change in applied voltages from the fourth duration to the fifth duration;
- $I_c$ may be a current output measured proximate an inflection of the output current transient due to a change in applied voltages from the fifth duration to the sixth duration;
- $I_d$ may be a current output measured proximate an inflection of the output current transient due to a change in applied voltages from the sixth duration to the seventh duration;
- $I_e$ may be a current output measured after the sixth duration but less than 10 seconds after a start of the test sequence;
- $x_1$ may be about 1.190;
- $x_2$ may be about 1.280;
- $x_3$ may be about 5.905;
- $x_4$ may be about 53.01;
- $x_5$ may be about 2.473.

In another variation, the glucose calculation of step 710 can be performed with Equation 4 of the following form:

$$g = x_1 \log\left( x_2 \left| \frac{I_c}{I_b} \right| \right) \otimes |I_e| + x_3$$ Equation 4 where:
- g is glucose concentration;
- $I_b$ may be a current output measured proximate an inflection of the output current transient due to a change in applied voltages from the fourth duration to the fifth duration;
- $I_c$ may be a current output measured proximate an inflection of the output current transient due to a change in applied voltages from the fifth duration to the sixth duration;
- $I_e$ may be a current output measured after the sixth duration but less than 10 seconds after a start of the test sequence;
- $x_1$ may be about 1.569;
- $x_2$ may be about 2.080; and
- $x_3$ may be about −2.661.

Furthermore, the glucose calculation can be performed with Equation 5 of the following form:

$$g = \left| \frac{I_d}{I_a} \right|^{x_1} \otimes \left| \frac{|I_e| + x_4 |I_a| - 2|I_b|}{|I_e| + x_4 |I_a|} \right| \otimes I_e \otimes x_2 / x_3.$$ Equation 5 where:
- g is glucose concentration;
- $I_a$ may be a current output measured proximate an inflection of the output current transient due to a change in applied voltages from the second to the third durations;
- $I_b$ may be a current output measured proximate an inflection of the output current transient due to a change in applied voltages from the fourth duration to the fifth duration;
- $I_d$ may be a current output measured proximate an inflection of the output current transient due to a change in applied voltages from the sixth duration to the seventh duration;
- $I_e$ may be a current output measured after the sixth duration but less than 10 seconds after a start of the test sequence;
- $x_1$ may be about 1.580;
- $x_2$ may be about 0.142;
- $x_3$ may be about 3.260; and
- $x_4$ may be about 46.40.

It is noted here that the plurality of voltages V1 ... $V_N$ (where N~2, 3, 4 ... n) in FIG. 6A may include two voltages of equal magnitude (i.e., 1 millivolts) but opposite in polarity. Further, the plurality of durations for respective voltages may include second, third, fourth, fifth, sixth, and seventh durations after the first duration with each duration being the same or different depending on the operational parameters of the biosensor system. In the measurement or sampling of the current at the respective time points, the current measured at each time point may be a summation of current about each time point. For example, the first current output may be a summation of current outputs from about 0.8 seconds to about 1.1 seconds and preferably from about 0.9 second to about 1 second from initiation of a glucose measurement sequence; the second current output may be a summation of current outputs from about 2.3 seconds to about 2.6 seconds and preferably from about 2.4 seconds to about 2.5 seconds from initiation of a glucose measurement sequence; the third current output may be a summation of current outputs from about 3.3 seconds to about 3.6 seconds and preferably from about 3.4 seconds to about 3.5 seconds from initiation of a glucose measurement sequence; the fourth current output may be a summation of the current outputs from about 3.8 seconds to about 4.1 seconds and preferably from about 3.9 seconds to about 4 seconds from initiation of a glucose measurement sequence; the fifth current output may be a summation of current outputs from about 4.8 seconds to about 5.1 seconds and preferably from about 4.9 seconds to about 5 seconds from initiation of a glucose measurement sequence. A summation of the current output is preferred to maximize precision of the generated results. Moreover, the summation will assume a sampling frequency of about 20 Hz such that a 5 sec measurement acquires 100 current samples which are referred to as a transient, shown here in FIG. 6A.

Figure 7:
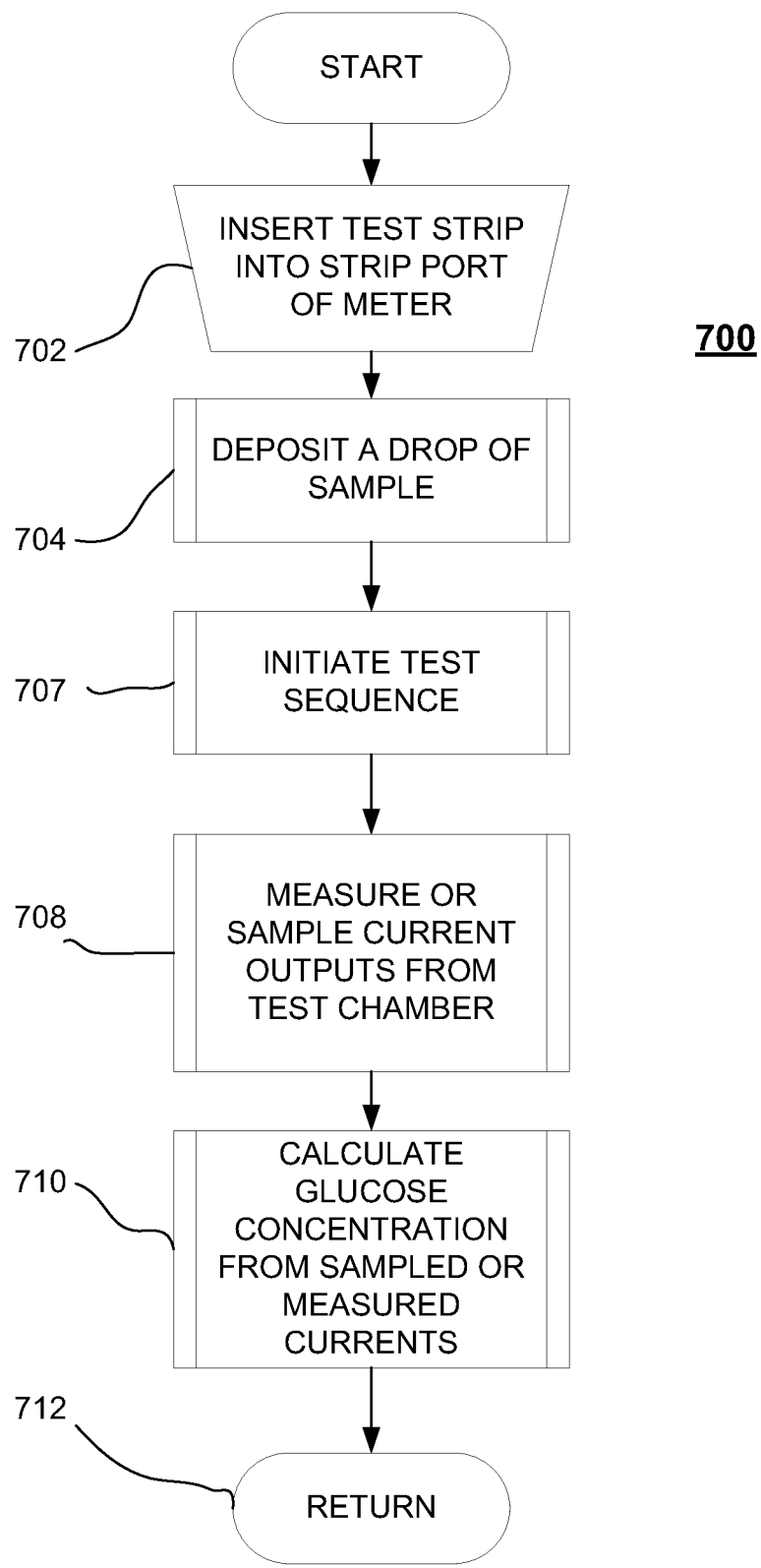
FIG. 7 is an exemplary logical flow chart of the techniques described herein.

Although step 706 in FIG. 7 has been described earlier, other variations are possible as part of this step. For example, other sub-steps can be utilized as part of this main step 706 to carry out the objectives of step 706. Specifically, the sub-steps may include applying a first voltage V1 of approximately ground potential to the test chamber for a first duration $t_1$ (FIG. 6A) so as to provide for a time delay, which is believed to allow the electrochemical reaction to initiate. The next sub-step may involve applying a second voltage V2 to the test chamber for a second duration $t_2$ (FIG. 6A) after the first duration $t_1$; changing the second voltage V2 to a third voltage V3 different from the second voltage V2 for a third duration $t_3$ after the second duration $t_2$; switching the third voltage V3 to a fourth voltage V4 different from the third voltage for a fourth duration $t_4$ after the third duration; altering the fourth voltage V4 to a fifth voltage V5 different from the fourth voltage V4 for a fifth duration $t_5$ after the fourth duration $t_4$; modifying the fifth voltage V5 to a sixth voltage V6 different from the fifth voltage for a sixth duration $t_6$ after the fifth duration $t_5$; changing the sixth voltage V6 to a seventh voltage V7 different from the sixth voltage V6 for a seventh duration $t_7$ after the sixth duration. At step 708, which could be performed in parallel with step 706, the system conducts a measurement of current outputs in the form of transient ($I_t$ in FIG. 6A).

Step 706 includes sub-steps such as, for example, measuring at least one of (a) a first current transient output ($I_a$) from the test chamber during a first interval Δ1 proximate the second and third durations; (b) a second current transient output ($I_b$) during a second interval Δ2 proximate the fourth and fifth durations; (c) a third current transient output ($I_c$) during a third interval Δ3 proximate the fifth and sixth durations; (d) a fourth current transient output ($I_d$) during a fourth interval Δ4 proximate the sixth and seventh durations; and (e) a fifth current transient output ($I_e$) during a fifth interval proximate the end of the seventh durations. It is noted here that each of the intervals Δ1 . . . Δ4 may include a very short time period (e.g., 10 milliseconds or less) during which the current transient is changing very rapidly to show an inflection in the transient. For example, first current output may be a summation of current outputs from about 0.8 seconds to about 1.1 seconds and preferably from about 0.9 second to about 1 second with respect to initiation of a test sequence voltage V1; the second current output may be a summation of current outputs from about 2.3 seconds to about 2.6 seconds and preferably from about 2.4 seconds to about 2.5 seconds with respect to initiation of the test sequence voltage; the third current output may be a summation of current outputs from about 3.3 seconds to about 3.6 seconds and preferably from about 3.4 seconds to about 3.5 seconds with respect to initiation of the test sequence voltage; the fourth current output may be a summation of the current outputs from about 3.8 seconds to about 4.1 seconds and preferably from about 3.9 seconds to about 4 seconds with respect to initiation of the test sequence voltage; the fifth current output may be a summation of current outputs from about 4.8 seconds to about 5.1 seconds and preferably from about 4.9 seconds to about 5 seconds with respect to initiation of the test sequence voltage.

Step 710 involves the calculating a glucose concentration of the sample. Applicants note that such calculation can be utilized with at least five different techniques (e.g., Equations 1-5) based on at least one of the first, second, third, fourth, or fifth current outputs such that bias in the glucose concentration is less than ±10% for 95% of glucose concentrations less than 75 mg/dL in hematocrits ranging from about 20% to about 60% shown here in FIGS. 9A-9E.

The techniques described herein were also validated by determining the bias or error between the calculated and reference glucose results, which are shown here in FIGS. 9A-9E. Each of FIGS. 9A to 9E will be discussed separately below. It is noted that the invention is not limited to one technique or one feature described herein but that all or some of the techniques (or features) can be combined in any suitable permutation, as long as each of the permutations function for its intended purpose of allowing for glucose determination with virtually no impact due to the physical characteristic(s) of the sample (e.g., hematocrit).

Figure 9A:
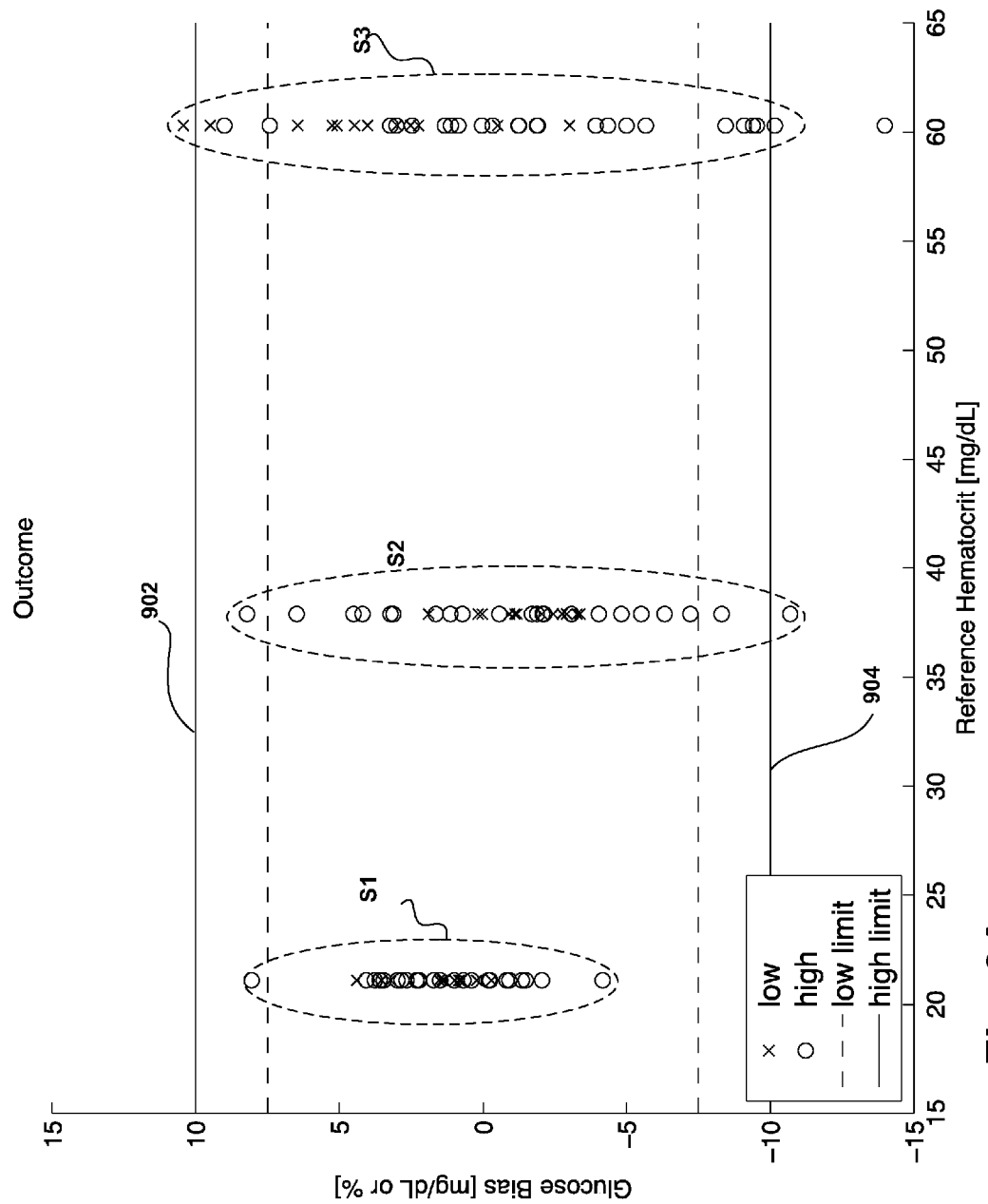
FIG. 9A illustrates bias or errors for three samples S1, S2, S3 (with different levels of hematocrits) as compared to referential glucose values using applicant's first technique to calculate glucose concentration that are generally insensitive to hematocrits.

Referring to FIG. 9A, applicant notes that the bias study of this figure was derived via exemplary Equation 1 for approximately 106 samples. In FIG. 9A, it can be seen that the samples S1, S2, S3 with glucose concentration of less than 75 mg/dL at respective 20%, 38%, or 60% hematocrits were within the bias of ±10% as defined by upper limit line 902 and lower limit line 904. The samples S1, S2, and S3 are generally within the upper limit 902 and lower limit 904, indicating that the glucose concentrations were not affected by the presence of varying levels of hematocrits for the technique using Equation 1.

Figure 9B:
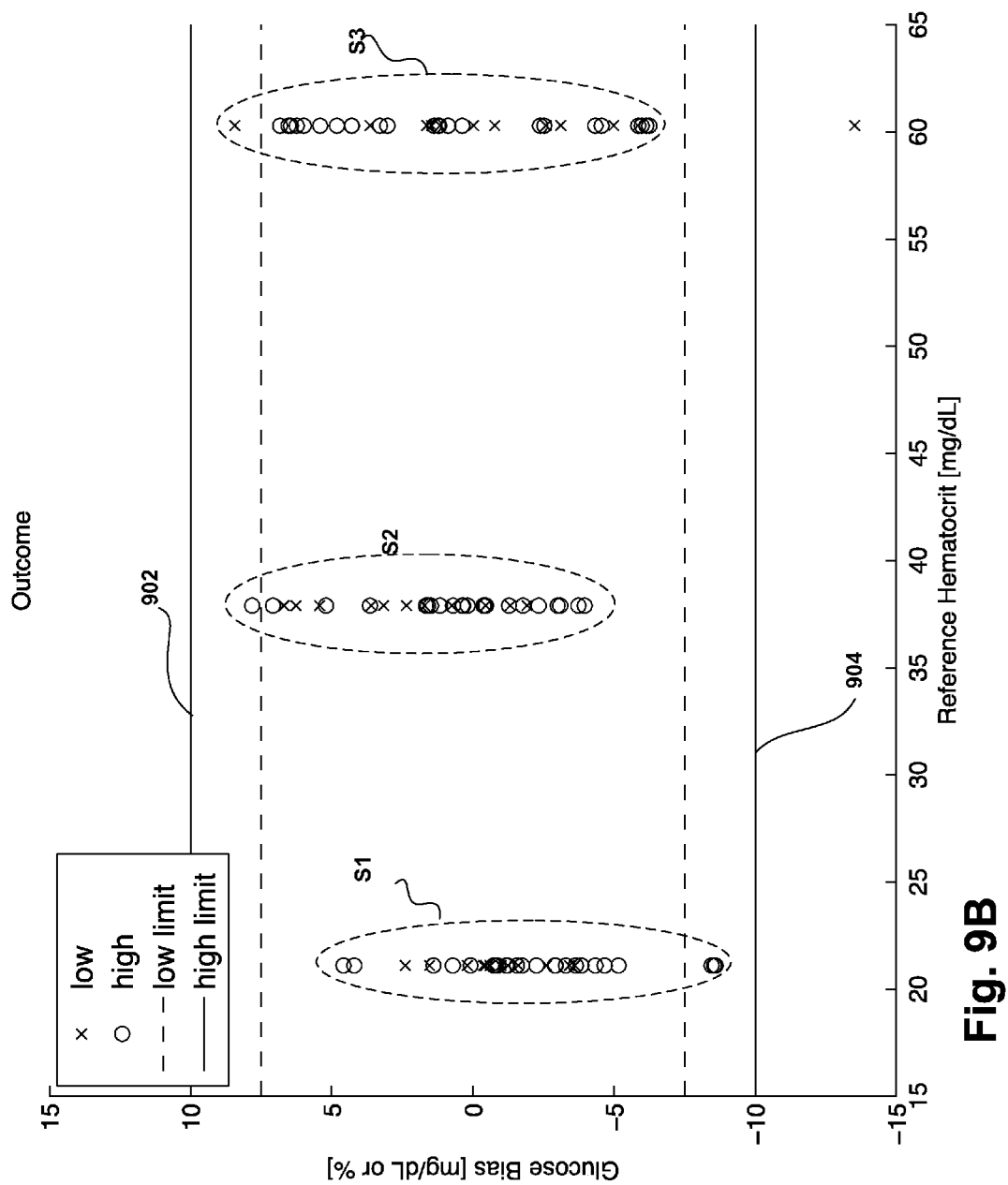
FIG. 9B illustrates bias or errors for three samples S1, S2, S3 (with different levels of hematocrits) as compared to referential glucose values using applicant's second technique to calculate glucose concentration that are generally insensitive to hematocrits.

Similarly, the results from 106 samples were derived with Equation 2 for FIG. 9B, where it can be seen that the samples S1, S2, S3 with glucose concentration of less than 75 mg/dL at respective 20%, 38%, or 60% hematocrits were generally within the bias of ±10% as defined by upper limit line 902 and lower limit line 904. Again, the measurements of samples S1, S2, and S3 are within the upper limit 902 and lower limit 904, indicating that the glucose concentrations were not affected by the presence of varying levels of hematocrits for the technique using Equation 2.

Figure 9C:
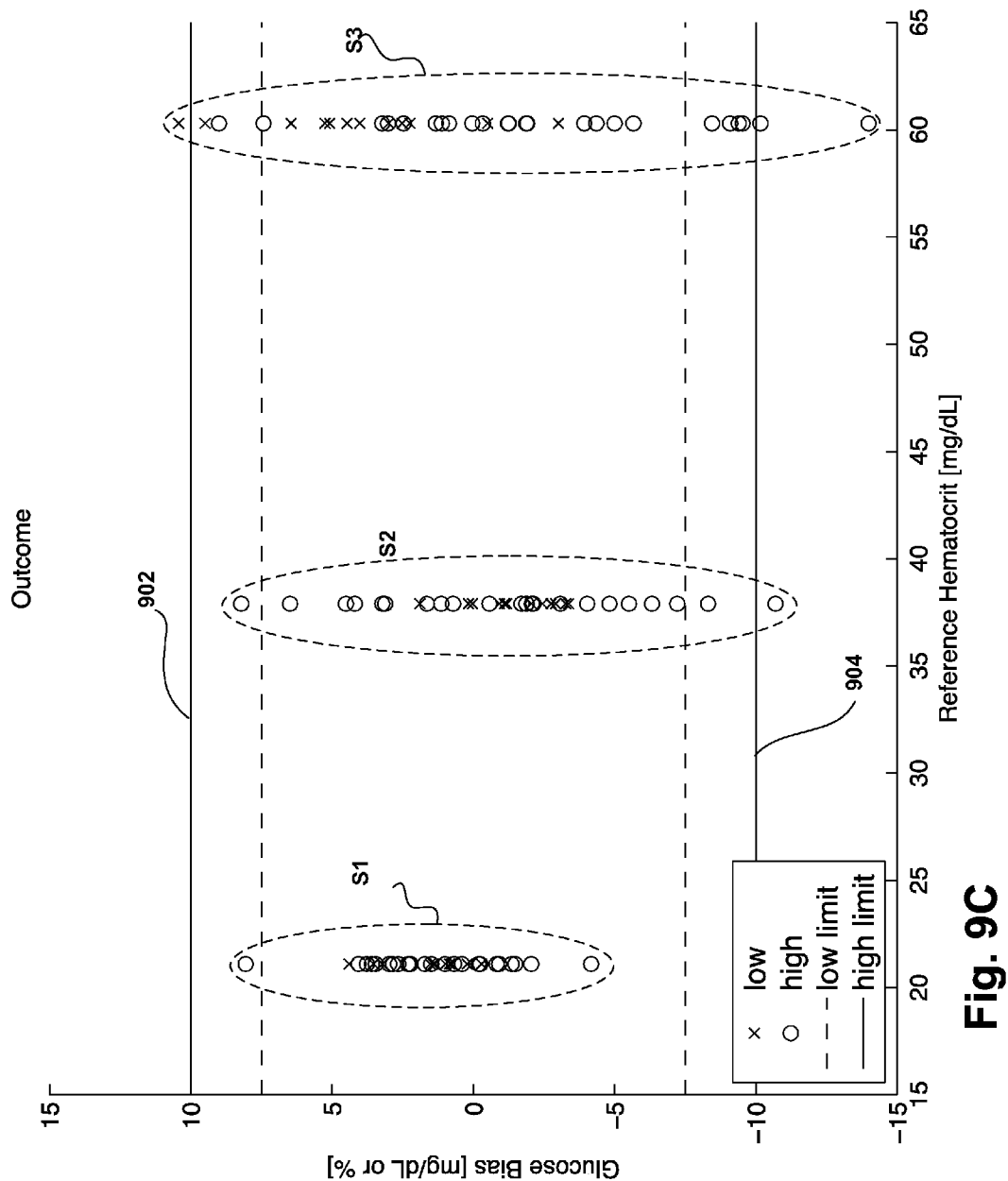
FIG. 9C illustrates bias or errors for three samples S1, S2, S3 (with different levels of hematocrits) as compared to referential glucose values using applicant's third technique to calculate glucose concentration that are generally insensitive to hematocrits.

Somewhat similar to FIGS. 9A and 9B, the use of Equation 3 for FIG. 9C shows that some of the glucose measurements in samples S3 with high hematocrits (e.g., 60%) are outside of the upper limit 902 and lower limit 904, indicating that the glucose concentrations of the samples were being affected by hematocrits at increasing percentage of hematocrits.

Figure 9D:
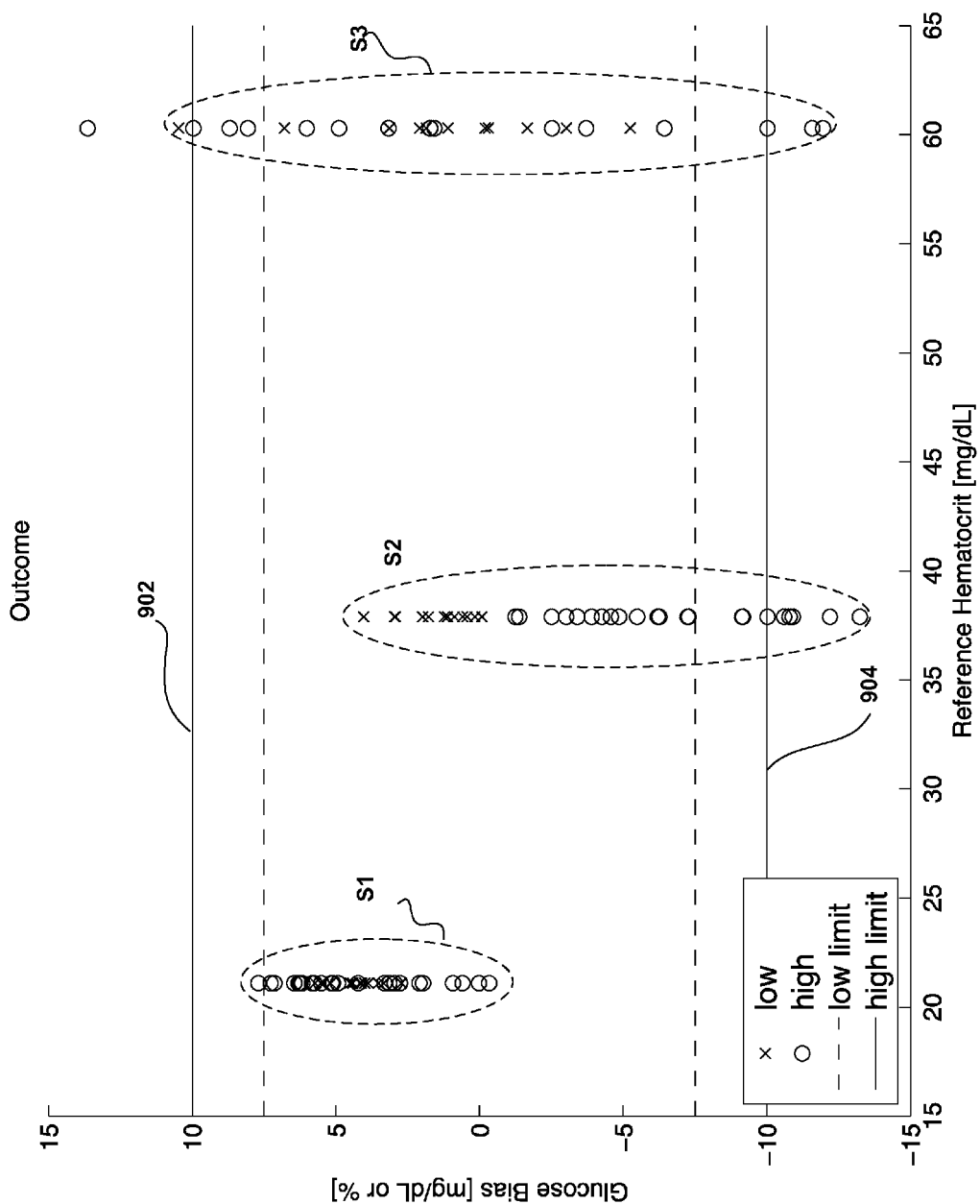
FIG. 9D illustrates bias or errors for three samples S1, S2, S3 (with different levels of hematocrits) as compared to referential glucose values using applicant's fourth technique to calculate glucose concentration that are generally insensitive to hematocrits.

Similarly, the use of Equation 4 indicates that the results were somewhat affected by hematocrits in FIG. 9D as shown by line 912 being affected by intermediate (38%) and high hematocrits (60%) present in the samples of groups S2 and S3.

Figure 9E:
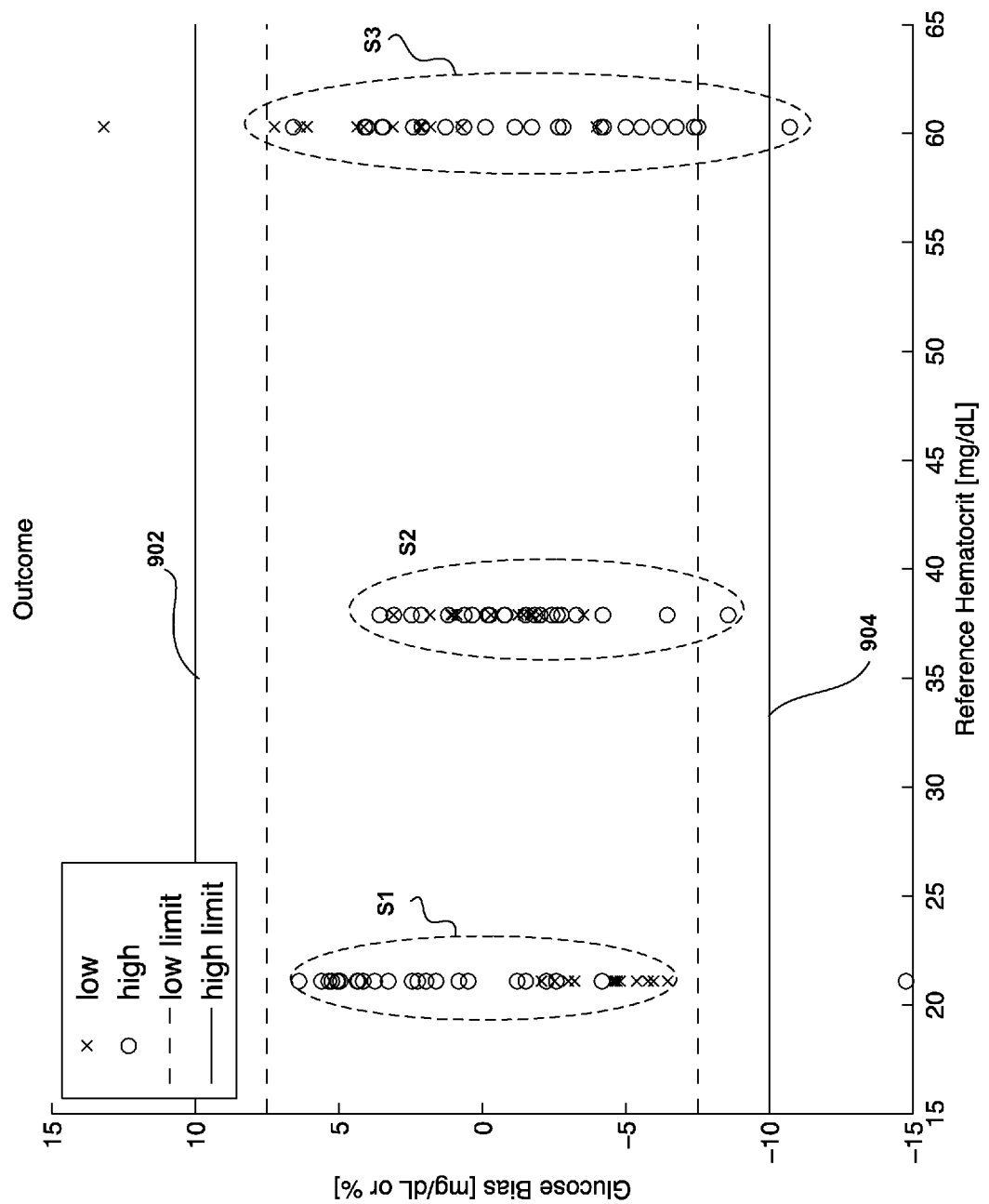
FIG. 9E illustrates bias or errors for three samples S1, S2, S3 (with different levels of hematocrits) as compared to referential glucose values using applicant's fifth technique to calculate glucose concentration that are generally insensitive to hematocrits.

Finally, the use of Equation 5 indicates that the results were slightly affected by at the high hematocrits (e.g., 60%) in FIG. 9E for samples in group S3.

Although the calculating of the glucose concentration has been shown based on five separate equations, other alternatives are also utilized. For example, the logic may compute glucose concentration using all five equations and then computing an average glucose concentration from all five results. Alternatively, the system may include provision to sense for hematocrits, and upon detection of high or low levels of hematocrit, the system may select only one or more of the equations to calculate the glucose concentration.

While the invention has been described in terms of particular variations and illustrative figures, those of ordinary skill in the art will recognize that the invention is not limited to the variations or figures described. In addition, where methods and steps described above indicate certain events occurring in certain order, those of ordinary skill in the art will recognize that the ordering of certain steps may be modified and that such modifications are in accordance with the variations of the invention. Additionally, certain of the steps may be performed concurrently in a parallel process when possible, as well as performed sequentially as described above. Therefore, to the extent there are variations of the invention, which are within the spirit of the disclosure or equivalent to the inventions found in the claims, it is the intent that this patent will cover those variations as well.

What is claimed is:

1. A method of determining blood glucose concentration with a glucose measurement system that comprises a test strip and test meter, the test meter having a microcontroller configured to apply a plurality of test voltages to the test strip and measure at least a current transient output resulting from an electrochemical reaction in a test chamber of the test strip, the method comprising:
    inserting the test strip into a strip port connector of the test meter to connect at least two electrodes coupled to the test chamber of the test strip to a strip measurement circuit;
    initiating a test sequence after deposition of a sample, in which the initiating comprises:
        applying a first voltage of approximately ground potential to the test chamber for a first duration;
        applying a second voltage to the test chamber for a second duration after the first duration;
        changing the second voltage to a third voltage different from the second voltage for a third duration after the second duration;
        switching the third voltage to a fourth voltage different from the third voltage for a fourth duration after the third duration;
        altering the fourth voltage to a fifth voltage different from the fourth voltage for a fifth duration after the fourth duration;
        modifying the fifth voltage to a sixth voltage different from the fifth voltage for a sixth duration after the fifth duration;
        changing the sixth voltage to a seventh voltage different from the sixth voltage for a seventh duration after the sixth duration, wherein each of the second to seventh voltages comprises about one millivolt;
    measuring at least one of:
        a first current transient output from the test chamber during a first interval proximate the second and third durations;
        a second current transient output during a second interval proximate the fourth and fifth durations;
        a third current transient output during a third interval proximate the fifth and sixth durations;
        a fourth current transient output during a fourth interval proximate the sixth and seventh durations; and
        a fifth current transient output during a fifth interval proximate the end of the seventh durations;
    calculating a glucose concentration of the sample from at least one of the first, second, third, fourth, or fifth current outputs such that bias in the glucose concentration is less than ±10% for glucose concentrations less than 75 mg/dL in hematocrits ranging from about 20% to about 60%.

2. The method of claim 1, in which the second voltage comprises a voltage opposite in polarity to the third, fifth and seventh voltages and with the same polarity as the fourth and sixth voltages.

3. The method of claim 1, in which the calculating comprises utilizing an equation of the form:

$$g = \left( x_1 |I_a|^{\left(x_2 - \frac{x_3}{|I_d|}\right)} \otimes x_4 |I_e| - x_5 \right) \Big/ x_6$$

where:
    g is glucose concentration;
    $I_a$ comprises a current output measured proximate an inflection of the output current transient due to a change in applied voltages from the second to the third durations;
    $I_d$ comprises a current output measured proximate an inflection of the output current transient due to a change in applied voltages from the sixth duration to the seventh duration;
    $I_e$ comprises a current output measured after the sixth duration but less than 10 seconds after a start of the test sequence;
    $x_1$ comprises about 203.9;
    $x_2$ comprises about −0.853;
    $x_3$ comprises about 20.21;
    $x_5$ comprises about −100.3; and
    $x_6$ comprises about 13.04.

4. The method of claim 1, in which the calculating comprises utilizing an equation of the form $$g = \left( \left| \frac{I_b}{I_3} \right|^{\left(x_1 - x_2 \left| \frac{I_d}{I_c} \right|\right)} \otimes x_3 \left| \frac{I_a}{I_d} \right|^{x_4} - x_5 \right) \Big/ x_6$$

where:
    g is glucose concentration;
    $I_a$ comprises a current output measured proximate an inflection of the output current transient due to a change in applied voltages from the second to the third durations;
    $I_b$ comprises a current output measured proximate an inflection of the output current transient due to a change in applied voltages from the fourth duration to the fifth duration;
    $I_c$ comprises a current output measured proximate an inflection of the output current transient due to a change in applied voltages from the fifth duration to the sixth duration;
    $I_d$ comprises a current output measured proximate an inflection of the output current transient due to a change in applied voltages from the sixth duration to the seventh duration;

I$_e$ comprises a current output measured after the sixth duration but less than 10 seconds after a start of the test sequence;
x$_1$ comprises about −1.114;
x$_2$ comprises about −1.930;
x$_3$ comprises about 74.23;
x$_4$ comprises about −1.449;
x$_5$ comprises about 275.0; and
x$_6$ comprises about 7.451.

5. The method of claim 1, in which the calculating comprises utilizing an equation of the form $$g = \left( \left| \frac{I_b}{I_a} \right|^{(x_1 - x_2 |I_e^{I_d}|)} \otimes x_3 I_c - x_4 \right) / x_5$$

Where:
g is glucose concentration;
I$_a$ comprises a current output measured proximate an inflection of the output current transient due to a change in applied voltages from the second to the third durations;
I$_b$ comprises a current output measured proximate an inflection of the output current transient due to a change in applied voltages from the fourth duration to the fifth duration;
I$_c$ comprises a current output measured proximate an inflection of the output current transient due to a change in applied voltages from the fifth duration to the sixth duration;
I$_d$ comprises a current output measured proximate an inflection of the output current transient due to a change in applied voltages from the sixth duration to the seventh duration;
I$_e$ comprises a current output measured after the sixth duration but less than 10 seconds after a start of the test sequence;
x$_1$ comprises about 1.190;
x$_2$ comprises about 1.280;
x$_3$ comprises about 5.905;
x$_4$ comprises about 53.01; and
x$_5$ comprises about 2.473.

6. The method of claim 1, in which the calculating comprises utilizing an equation of the form $$g = x_1 \log\left( x_2 \left| \frac{I_c}{I_b} \right| \right) \otimes |I_e| + x_3$$

where:
g is glucose concentration;
I$_b$ comprises a current output measured proximate an inflection of the output current transient due to a change in applied voltages from the fourth duration to the fifth duration;
I$_c$ comprises a current output measured proximate an inflection of the output current transient due to a change in applied voltages from the fifth duration to the sixth duration;
I$_e$ comprises a current output measured after the sixth duration but less than 10 seconds after a start of the test sequence;
x$_1$ comprises about 1.569;
x$_2$ comprises about 2.080; and
x$_3$ comprises about −2.661.

7. The method of claim 1, in which the calculating comprises utilizing an equation of the form $$g = \left| \frac{I_d}{I_a} \right|^{x_1} \otimes \left| \frac{|I_e| + x_4 |I_a| - 2|I_b|}{|I_e| + x_4 |I_a|} \right| \otimes I_e \right| \otimes x_2 / x_3$$

where:
g is glucose concentration;
I$_a$ comprises a current output measured proximate an inflection of the output current transient due to a change in applied voltages from the second to the third durations;
I$_b$ comprises a current output measured proximate an inflection of the output current transient due to a change in applied voltages from the fourth duration to the fifth duration;
I$_d$ comprises a current output measured proximate an inflection of the output current transient due to a change in applied voltages from the sixth duration to the seventh duration;
I$_e$ comprises a current output measured after the sixth duration but less than 10 seconds after a start of the test sequence;
x$_1$ comprises about 1.580;
x$_2$ comprises about 0.142;
x$_3$ comprises about 3.260; and
x$_4$ comprises about 46.40.

8. A method of determining blood glucose concentration with a glucose measurement system that comprises a test strip and test meter, the test meter having a microcontroller configured to apply a plurality of test voltages to the test strip and measure at least a current transient output resulting from an electrochemical reaction in a test chamber of the test strip, the method comprising:
inserting the test strip into a strip port connector of the test meter to connect at least two electrodes coupled to the test chamber of the test strip to a strip measurement circuit;
initiating a test sequence after deposition of a sample, in which the initiating comprises:
applying a zero potential for a first duration to the test chamber;
driving a plurality of voltages to the test chamber over a plurality of durations after the first duration in which at least one millivolt for one duration is opposite in polarity to another voltage in another duration after the one duration such that the change in polarity produces a plurality of inflections in a current output transient of the test chamber;
measuring magnitudes of the current output transient proximate respective inflections of the current transient caused by the change in polarity in the plurality of voltages, wherein the plurality of voltages comprises two voltages of equal magnitude but opposite in polarity; and the measuring comprises summing current outputs of a decay of the current transient during an interval proximate the decay of the current transient; and
calculating a glucose concentration of the sample from magnitudes of the current transient of the measuring step.

9. The method of claim 8, in which the plurality of durations comprises second, third, fourth, fifth, sixth, and seventh durations after the first duration.

10. The method of claim 9, in which the calculating comprises utilizing an equation of the form:

$$g = \left(x_1 |I_a|^{\left(x_2 - \frac{x_3}{|I_d|}\right)} \otimes x_4 |I_e| - x_5\right) / x_6$$

where:
g is glucose concentration;
$I_a$ comprises a current output measured proximate an inflection of the output current transient due to a change in applied voltages from the second to the third durations;
$I_d$ comprises a current output measured proximate an inflection of the output current transient due to a change in applied voltages from the sixth duration to the seventh duration;
$I_e$ comprises a current output measured after the sixth duration but less than 10 seconds after a start of the test sequence;
$x_1$ comprises about 203.9;
$x_2$ comprises about −0.853;
$x_3$ comprises about 20.21;
$x_5$ comprises about −100.3; and
$x_6$ comprises about 13.04.

11. The method of claim 9, in which the calculating comprises utilizing an equation of the form $$g = \left(\left|\frac{I_b}{I_e}\right|^{\left(x_1 - x_2 \left|\frac{I_d}{I_c}\right|\right)} \otimes x_3 \left|\frac{I_a}{I_d}\right|^{x_4} - x_5\right) / x_6$$

Where
g is glucose concentration;
$I_a$ comprises a current output measured proximate an inflection of the output current transient due to a change in applied voltages from the second to the third durations;
$I_b$ comprises a current output measured proximate an inflection of the output current transient due to a change in applied voltages from the fourth duration to the fifth duration;
$I_c$ comprises a current output measured proximate an inflection of the output current transient due to a change in applied voltages from the fifth duration to the sixth duration;
$I_d$ comprises a current output measured proximate an inflection of the output current transient due to a change in applied voltages from the sixth duration to the seventh duration;
$I_e$ comprises a current output measured after the sixth duration but less than 10 seconds after a start of the test sequence;
$x_1$ comprises about −1.114;
$x_2$ comprises about −1.930;
$x_3$ comprises about 74.23;
$x_4$ comprises about −1.449;
$x_5$ comprises about 275.0; and
$x_6$ comprises about 7.451.

12. The method of claim 9, in which the calculating comprises utilizing an equation of the form $$g = \left(\left|\frac{I_b}{I_a}\right|^{\left(x_1 - x_2 \left|\frac{I_d}{I_e}\right|\right)} \otimes x_3 I_c - x_4\right) / x_5$$

Where:
g is glucose concentration;
$I_a$ comprises a current output measured proximate an inflection of the output current transient due to a change in applied voltages from the second to the third durations;
$I_b$ comprises a current output measured proximate an inflection of the output current transient due to a change in applied voltages from the fourth duration to the fifth duration;
$I_c$ comprises a current output measured proximate an inflection of the output current transient due to a change in applied voltages from the fifth duration to the sixth duration;
$I_d$ comprises a current output measured proximate an inflection of the output current transient due to a change in applied voltages from the sixth duration to the seventh duration;
$I_e$ comprises a current output measured after the sixth duration but less than 10 seconds after a start of the test sequence;
$x_1$ comprises about 1.190;
$x_2$ comprises about 1.280;
$x_3$ comprises about 5.905;
$x_4$ comprises about 53.01; and
$x_5$ comprises about 2.473.

13. The method of claim 9, in which the calculating comprises utilizing an equation of the form $$g = x_1 \log\left(x_2 \left|\frac{I_c}{I_b}\right|\right) \otimes |I_e| + x_3$$

where:
g is glucose concentration;
$I_b$ comprises a current output measured proximate an inflection of the output current transient due to a change in applied voltages from the fourth duration to the fifth duration;
$I_c$ comprises a current output measured proximate an inflection of the output current transient due to a change in applied voltages from the fifth duration to the sixth duration;
$I_e$ comprises a current output measured after the sixth duration but less than 10 seconds after a start of the test sequence;
$x_1$ comprises about 1.569;
$x_2$ comprises about 2.080; and
$x_3$ comprises about −2.661.

14. The method of claim 9, in which the calculating comprises utilizing an equation of the form $$g = \left|\frac{I_d}{I_a}\right|^{x_1} \otimes \left|\frac{|I_e| + x_4 |I_a| - 2|I_b|}{|I_e| + x_4 |I_a|} \otimes I_e\right| \otimes x_2 / x_3$$

where:
g is glucose concentration;
$I_a$ comprises a current output measured proximate an inflection of the output current transient due to a change in applied voltages from the second to the third durations;
$I_b$ comprises a current output measured proximate an inflection of the output current transient due to a change in applied voltages from the fourth duration to the fifth duration;

$I_d$ comprises a current output measured proximate an inflection of the output current transient due to a change in applied voltages from the sixth duration to the seventh duration;

$I_e$ comprises a current output measured after the sixth duration but less than 10 seconds after a start of the test sequence;

$x_1$ comprises about 1.580;
$x_2$ comprises about 0.142;
$x_3$ comprises about 3.260; and
$x_4$ comprises about 46.40.

15. A blood glucose measurement system comprising:
an analyte test strip including:
a substrate having a reagent disposed thereon;
at least two electrodes proximate the reagent in a test chamber;
an analyte meter including:
a strip port connector disposed to connect to the two electrodes;
a power supply; and
a microcontroller electrically coupled to the strip port connector and the power supply so that, when the test strip is inserted into the strip port connector and a blood sample is deposited in the test chamber for chemical transformations of glucose in the blood sample, a glucose concentration of the blood sample is determined by the microcontroller from at least one of the first, second, third, fourth, or fifth current outputs from the test chamber due to applied voltages such that bias in the glucose concentration is less than ±10% for glucose concentrations less than 75 mg/dL in hematocrits ranging from about 20% to about 60%, in which the microcontroller calculates glucose concentration with an equation of the form:
utilizing an equation of the form $$g = \left(x_1 |I_a|^{\left(x_2 - \frac{x_3}{|I_d|}\right)} \otimes x_4 |I_e| - x_5\right) / x_6$$

where:
g is glucose concentration;
$I_a$ comprises a current output measured proximate an inflection of the output current transient due to a change in applied voltages from the second to the third durations;
$I_d$ comprises a current output measured proximate an inflection of the output current transient due to a change in applied voltages from the sixth duration to the seventh duration;
$I_e$ comprises a current output measured after the sixth duration but less than 10 seconds after a start of the test sequence;
$x_1$ comprises about 203.9;
$x_2$ comprises about −0.853;
$x_3$ comprises about 20.21;
$x_5$ comprises about −100.3; and
$x_6$ comprises about 13.04.

16. A blood glucose measurement system comprising:
an analyte test strip including:
a substrate having a reagent disposed thereon;
at least two electrodes proximate the reagent in a test chamber;
an analyte meter including:
a strip port connector disposed to connect to the two electrodes;
a power supply; and
a microcontroller electrically coupled to the strip port connector and the power supply so that, when the test strip is inserted into the strip port connector and a blood sample is deposited in the test chamber for chemical transformations of glucose in the blood sample, a glucose concentration of the blood sample is determined by the microcontroller from at least one of the first, second, third, fourth, or fifth current outputs from the test chamber due to applied voltages such that bias in the glucose concentration is less than ±10% for glucose concentrations less than 75 mg/dL in hematocrits ranging from about 20% to about 60%, which the microcontroller calculates glucose concentration with an equation of the form:

$$g = \left(\left|\frac{I_b}{I_e}\right|^{\left(x_1 - x_2 \left|\frac{I_d}{I_c}\right|\right)} \otimes x_3 \left|\frac{I_a}{I_d}\right|^{x_4} - x_5\right) / x_6$$

where:
g is glucose concentration;
$I_a$ comprises a current output measured proximate an inflection of the output current transient due to a change in applied voltages from the second to the third durations;
$I_b$ comprises a current output measured proximate an inflection of the output current transient due to a change in applied voltages from the fourth duration to the fifth duration;
$I_c$ comprises a current output measured proximate an inflection of the output current transient due to a change in applied voltages from the fifth duration the sixthe sixth duration;
$I_d$ comprises a current output measured proximate an inflection of the output current transient due to a change in applied voltages from the sixth duration to the seventh duration;
$I_e$ comprises a current output measured after the sixth duration but less than 10 seconds after a start of the test sequence;
$x_1$ comprises about −1.114;
$x_2$ comprises about −1.930;
$x_3$ comprises about 74.23;
$x_4$ comprises about −1.449;
$x_5$ comprises about 275.0; and
$x_6$ comprises about 7.451.

* * * * *

UNITED STATES PATENT AND TRADEMARK OFFICE
CERTIFICATE OF CORRECTION

PATENT NO. : 9,005,426 B1
APPLICATION NO. : 13/630334
DATED : April 14, 2015
INVENTOR(S) : Michael Malecha Page 1 of 1

It is certified that error appears in the above-identified patent and that said Letters Patent is hereby corrected as shown below:

In Claim 4, Column 18, line 47, please change "$I_3$" in the formula to --$I_e$--.

Signed and Sealed this
Fifteenth Day of March, 2016

Michelle K. Lee
*Director of the United States Patent and Trademark Office*